US012612372B2

(12) United States Patent
Pae et al.

(10) Patent No.: US 12,612,372 B2
(45) **Date of Patent: *Apr. 28, 2026**

(54) OXOPYRIDAZINYL-PHENYL-CARBONOHYDRAZONOYL DICYANIDE COMPOUND AND USE THEREOF

(71) Applicant: KOREA INSTITUTE OF SCIENCE AND TECHNOLOGY, Seoul (KR)

(72) Inventors: Ae Nim Pae, Seoul (KR); Yun Kyung Kim, Seoul (KR); Sang Min Lim, Seoul (KR); Sungsu Lim, Seoul (KR); Haeun Lee, Seoul (KR); Woo Seung Son, Seoul (KR); Hye Yeon Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 581 days.

This patent is subject to a terminal disclaimer.

(21) Appl. No.: 18/011,460

(22) PCT Filed: Jun. 18, 2021

(86) PCT No.: PCT/KR2021/007692

§ 371 (c)(1),
(2) Date: Dec. 19, 2022

(87) PCT Pub. No.: WO2021/256900

PCT Pub. Date: Dec. 23, 2021

(65) Prior Publication Data

US 2023/0278963 A1 Sep. 7, 2023

(30) Foreign Application Priority Data

Jun. 19, 2020 (KR) ........................ 10-2020-0075040

(51) Int. Cl.

| | |
|---|---|
| ***C07D 217/24*** | (2006.01) |
| ***C07D 215/227*** | (2006.01) |
| ***C07D 235/26*** | (2006.01) |
| ***C07D 237/14*** | (2006.01) |
| ***C07D 263/58*** | (2006.01) |
| ***C07D 277/68*** | (2006.01) |
| ***C07D 471/04*** | (2006.01) |

(52) U.S. Cl.
CPC .................................. *C07D 237/14* (2013.01)

(58) Field of Classification Search
CPC .................................................... C07D 237/14
See application file for complete search history.

(56) References Cited

U.S. PATENT DOCUMENTS

| | | | | |
|---|---|---|---|---|
| 5,019,575 | A * | 5/1991 | Haikala | A61P 9/04 544/239 |
| 9,962,384 | B1 | 5/2018 | Kim et al. | |
| 2014/0107125 | A1 | 4/2014 | Zhang et al. | |
| 2022/0396553 | A1 * | 12/2022 | Pae | C07D 471/04 |
| 2023/0278965 | A1 * | 9/2023 | Pae | C07D 413/12 514/255.05 |
| 2023/0295095 | A1 * | 9/2023 | Pae | A61P 27/06 514/300 |

FOREIGN PATENT DOCUMENTS

| | | | | |
|---|---|---|---|---|
| CN | 104418810 A | | 3/2015 | |
| CN | 104987310 A | | 10/2015 | |
| CN | 112500353 | * | 3/2021 | C07F 9/6509 |
| EP | 3 424 908 A1 | | 10/2017 | |
| KR | 10-2012-0090940 A | | 8/2012 | |
| KR | 10-2018-0050130 A | | 5/2018 | |
| KR | 10-2020-0076808 A | | 6/2020 | |
| WO | WO 2020/041180 A1 | | 2/2020 | |
| WO | WO-2020130214 A1 | * | 6/2020 | C07D 417/12 |

OTHER PUBLICATIONS

Alzheimer's Association "Can Alzheimer's Disease Be Prevented?" Downloaded Jun. 11, 2025 from https://www.alz.org/alzheimers-dementia/research-and-progress/prevention (Year: 2025).*
National Center for Biotechnology Information. PubChem Substance Record for SID 39218904, SID 39218904, Source: ChemSpider. https://pubchem.ncbi.nlm.nih.gov/substance/39218904. Available Dec. 5, 2007. (Year: 2007).*
Japanese Office Action issued on Jan. 16, 2024, in counterpart Japanese Patent Application No. 2022-577313 (2 pages in Japanese).
Pineda-Sanabria, S. E. et al., "Probing the mechanism of cardiovascular drugs using a covalent levosimendan analog", Journal of Molecular and Cellular Cardiology 92 (Feb. 14, 2016) pp. 174-184.
Crowe, A. et al., "Compound screening in cell-based models of tau inclusion formation: Comparison of primary neuron and HEK293 cell assays", Journal of Biological Chemistry, Feb. 7, 2020, 295, 12, pp. 4001-4013.

* cited by examiner

*Primary Examiner* — Daniel R Carcanague
(74) *Attorney, Agent, or Firm* — NSIP Law

(57) ABSTRACT

Provided are novel oxopyridazinyl-phenyl-carbonohydrazonoyl dicyanide compounds and uses thereof.

15 Claims, No Drawings

OXOPYRIDAZINYL-PHENYL-CARBONOHYDRAZONOYL DICYANIDE COMPOUND AND USE THEREOF

CROSS-REFERENCE TO RELATED APPLICATIONS

This application is a U.S. national stage application of International Application No. PCT/KR2021/007692 filed on Jun. 18, 2021, which claims the benefit under 35 USC 119 (a) and 365 (b) of Korean Patent Application No. 10-2020-0075040 filed on Jun. 19, 2020, in the Korean Intellectual Property Office, the entire disclosures of which are incorporated herein by reference for all purposes.

TECHNICAL FIELD

The present invention relates to novel oxopyridazinyl-phenyl-carbonohydrazonoyl dicyanide compounds and uses thereof.

BACKGROUND ART

Tau protein (tau (τ) protein), which is a microtubule-associated protein (MAP) mainly expressed in axons of nerve cells with a molecular weight of 50,000 to 70,000, serves to stabilize microtubules, and represents molecular diversity through phosphorylation. In humans, tau protein is formed into six isoforms by the insertion of 29 or 58 amino acid residues at the N-terminus and the alternative splicing of mRNA of 3 or 4 repeating structures (referred to as microtubule binding domain) at the C-terminus.

In healthy nerves, tau protein stabilizes microtubules by promoting growth from axons and nerve cell polarization. When pathological hyperphosphorylation occurs, tau protein separates from microtubules, resulting in insoluble aggregation. Further, a structural skeleton inducing the aggregation of tau protein has been proposed, and evidence has been provided that insoluble filaments are formed from 10 soluble monomers, and that these filaments are bound into high-dimensional structures called neurofibrillary tangles (NFTs). Human full-length tau protein includes a microtubule binding domain consisting of four repetitive conserved sequences. Among these repetitive sequences, positively charged residues have an important function in binding to highly negatively charged microtubules (20 to 30 electrons per αβ-tubulin dimer). The binding affinity to tau microtubules is also actively regulated by the phosphorylation of tau protein, and this phosphorylation causes dynamic rearrangement of microtubule networks. When tau protein is phosphorylated abnormally excessively, the balance of this dynamic rearrangement is disrupted, and the affinity to microtubules is rapidly decreased.

The hyperphosphorylation and/or aggregation of tau proteins cause abnormal accumulation of these tau proteins in nerve cells, which is pointed to as a cause of various neurodegenerative diseases and the like. Tau protein aggregates are mainly found in the cell bodies and dendrites of nerve cells, and these tau protein aggregates are called neurofibrillary tangles (NFTs) and neuropil threads. Examination of the microstructures of neurofibrillary tangles (NFTs) reveals that such microstructures thereof consist of paired helical filaments (PHFs) in which tau proteins are entangled like fine threads and are aggregated and hyperphosphorylated, unlike normal tau protein. An abnormal tau protein aggregation phenomenon appears also in tauopathy. In this case, although it is not known exactly what role the aggregation of tau protein plays in the progress of tauopathy, this tau protein aggregation phenomenon appears similar to an aggregation phenomenon that is common in general neurodegenerative diseases.

As such, although it is known that hyperphosphorylation and/or aggregation of tau protein causes various neurodegenerative diseases comprising Alzheimer's disease and tauopathy, the specific mechanism how these abnormal tau species cause changes in the signaling pathway and elicit neurotoxicity has not yet been verified, and there are no effective treatment methods or therapeutic agents yet available to treat these diseases.

DISCLOSURE

Technical Problem

As a result of intensive efforts to develop novel small-molecule compounds capable of inhibiting aggregation and/or hyperphosphorylation of tau protein, the present inventors have found that a series of novel oxopyridazinyl-phenyl-carbonohydrazonoyl dicyanide compounds effectively inhibit aggregation of tau protein without exhibiting cytotoxicity at effective concentrations, thereby completing the present invention.

Technical Solution

An object of the present invention is to provide a compound represented by Formula 1 below or a pharmaceutically acceptable salt thereof:

[Formula 1]

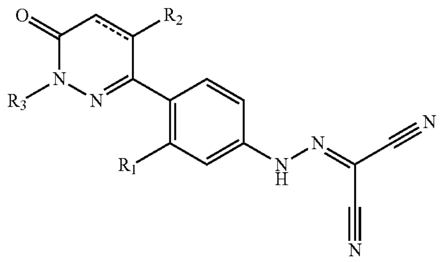

in Formula 1 above,

- - - - is —— or ═══;

$R_1$ is hydrogen or halogen;

$R_2$ is hydrogen or $C_{1-6}$ alkyl; and $R_3$ is $C_{1-6}$ alkyl, $C_{1-6}$ alkoxy-Cm alkyl, $C_{1-6}$ haloalkyl, $C_{3-6}$ cycloalkyl, or $C_{1-6}$ alkoxy-$C_{6-10}$ aryl.

Another object of the present invention is to provide a method of preparing the compound of the compound described above.

Still another object of the present invention is to provide a composition for inhibiting aggregation of tau protein including the compound described above as an active ingredient.

Still another object of the present invention is to provide a composition for inhibiting hyperphosphorylation of tau protein including the compound described above as an active ingredient.

Still another object of the present invention is to provide a pharmaceutical composition for preventing or treating a disease caused by aggregation or hyperphosphorylation of tau protein including the compound described above as an active ingredient.

Still another object of the present invention is to provide a method of preventing or treating a disease caused by aggregation or hyperphosphorylation of tau protein, the method including administering the pharmaceutical composition described above to a subject in need thereof.

Advantageous Effects

The novel oxopyridazinyl-phenyl-carbonohydrazonoyl dicyanide compounds of the present invention may effectively inhibit aggregation and/or hyperphosphorylation of tau protein, and thus may be effectively used in prevention or treatment of diseases caused thereby such as Alzheimer's disease and various tauopathies.

BEST MODE

A first aspect of the present invention is to provide a compound represented by Formula 1 below or a pharmaceutically acceptable salt thereof:

[Formula 1]

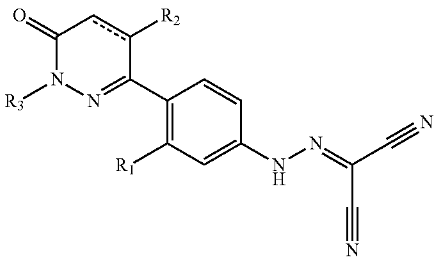

in Formula 1 above,

----- is —— or ═══;

$R_1$ is hydrogen or halogen;

$R_2$ is hydrogen or $C_{1-6}$ alkyl; and $R_3$ is $C_{1-6}$ alkyl, $C_{1-6}$ alkoxy-$C_{0-6}$ alkyl, $C_{1-6}$ haloalkyl, $C_{3-6}$ cycloalkyl, or $C_{1-6}$ alkoxy-$C_{6-10}$ aryl.

Specifically, in the compound of the present invention, $R_1$ is hydrogen, chloro, or fluoro;

$R_2$ is hydrogen or methyl; and $R_3$ is methyl, ethyl, isopropyl, cyclopropyl, difluoromethyl, 2,2,2-trifluoroethyl, methoxyphenyl, or methoxyethyl, but the present invention is not limited thereto.

For example, the compound of the present invention may be represented by Formula 2 or 3 below:

[Formula 2]

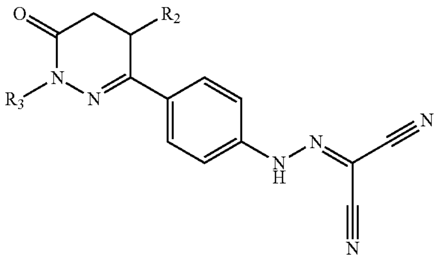

-continued

[Formula 3]

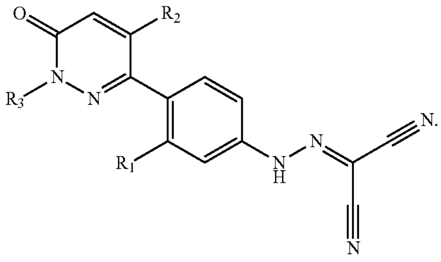

In Formula 2 or 3 above, substituents are as defined above.

More particularly, the compound may be 1. (4-(1-isopropyl-6-oxo-1,4,5,6-tetrahydropyridazin-3-yl)phenyl)carbonohydrazonoyl dicyanide,
2. (4-(1-isopropyl-4-methyl-6-oxo-1,4,5,6-tetrahydropyridazin-3-yl)phenyl)carbonohydrazonoyl dicyanide,
3. (4-(1-ethyl-4-methyl-6-oxo-1,4,5,6-tetrahydropyridazin-3-yl)phenyl)carbonohydrazonoyl dicyanide,
4. (4-(4-methyl-6-oxo-1-(2,2,2-trifluoroethyl)-1,4,5,6-tetrahydropyridazin-3-yl)phenyl)carbonohydrazonoyl dicyanide,
5. (4-(1-(2-methoxyethyl)-4-methyl-6-oxo-1,4,5,6-tetrahydropyridazin-3-yl)phenyl)carbonohydrazonoyl dicyanide,
6. (4-(1-cyclopropyl-4-methyl-6-oxo-1,4,5,6-tetrahydropyridazin-3-yl)phenyl)carbonohydrazonoyl dicyanide,
7. (4-(1-(4-methoxyphenyl)-4-methyl-6-oxo-1,4,5,6-tetrahydropyridazin-3-yl)phenyl)carbonohydrazonoyl dicyanide,
8. (4-(1-methyl-6-oxo-1,6-dihydropyridazin-3-yl)phenyl)carbonohydrazonoyl dicyanide,
9. (4-(1-isopropyl-6-oxo-1,6-dihydropyridazin-3-yl)phenyl)carbonohydrazonoyl dicyanide,
10. (4-(1-(difluoromethyl)-6-oxo-1,6-dihydropyridazin-3-yl)phenyl)carbonohydrazonoyl dicyanide,
11. (4-(1,4-dimethyl-6-oxo-1,6-dihydropyridazin-3-yl)phenyl)carbonohydrazonoyl dicyanide,
12. (4-(1-isopropyl-4-methyl-6-oxo-1,6-dihydropyridazin-3-yl)phenyl)carbonohydrazonoyl dicyanide,
13. (3-chloro-4-(1,4-dimethyl-6-oxo-1,6-dihydropyridazin-3-yl)phenyl)carbonohydrazonoyl dicyanide, or
14. (4-(1,4-dimethyl-6-oxo-1,6-dihydropyridazin-3-yl)-3-fluorophenyl)carbonohydrazonoyl dicyanide.

Furthermore, these compounds may be compounds represented by the formulae shown in Table 1 below.

TABLE 1

| | |
|---|---|
| 1 | 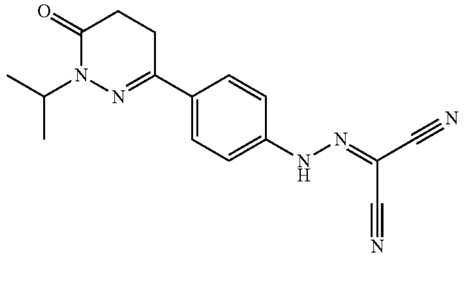 [SMILES: CC(C)N1N=C(c2ccc(NN=C(C#N)C#N)cc2)CCC1=O] |

TABLE 1-continued
2
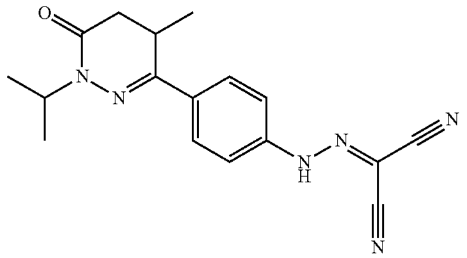 [SMILES: CC1CC(=O)N(C(C)C)N=C1c1ccc(NN=C(C#N)C#N)cc1]
3
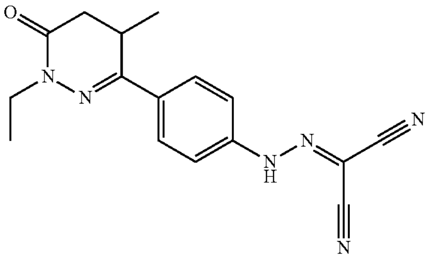 [SMILES: CCN1N=C(c2ccc(NN=C(C#N)C#N)cc2)C(C)CC1=O]
4
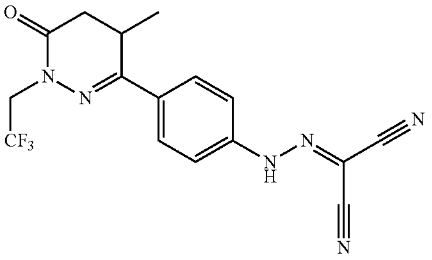 [SMILES: CC1CC(=O)N(CC(F)(F)F)N=C1c1ccc(NN=C(C#N)C#N)cc1]
5
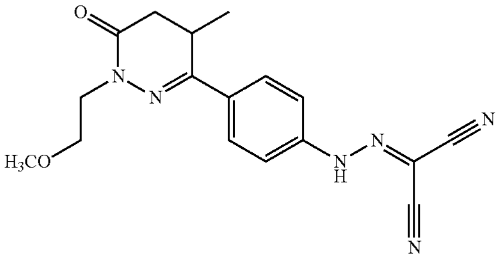 [SMILES: COCCN1N=C(c2ccc(NN=C(C#N)C#N)cc2)C(C)CC1=O]
6
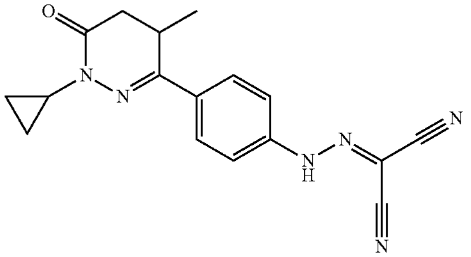 [SMILES: CC1CC(=O)N(C2CC2)N=C1c1ccc(NN=C(C#N)C#N)cc1]
7
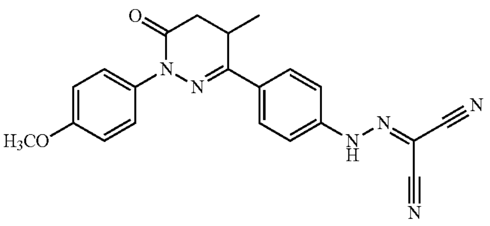 [SMILES: COc1ccc(N2N=C(c3ccc(NN=C(C#N)C#N)cc3)C(C)CC2=O)cc1]
TABLE 1-continued
8
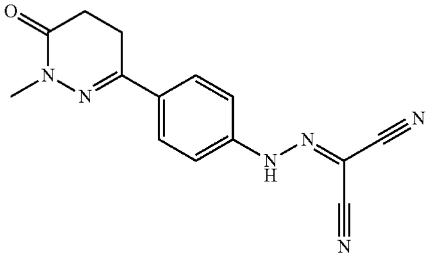 [SMILES: CN1N=C(c2ccc(NN=C(C#N)C#N)cc2)CCC1=O]
9
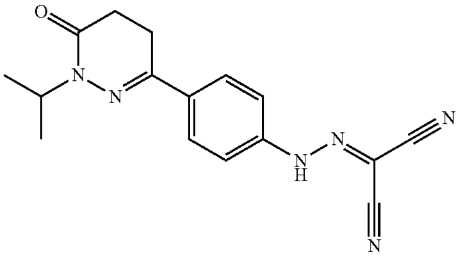 [SMILES: CC(C)N1N=C(c2ccc(NN=C(C#N)C#N)cc2)CCC1=O]
10
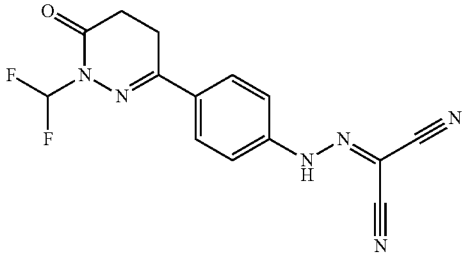 [SMILES: N#CC(C#N)=NNc1ccc(C2=NN(C(F)F)C(=O)CC2)cc1]
11
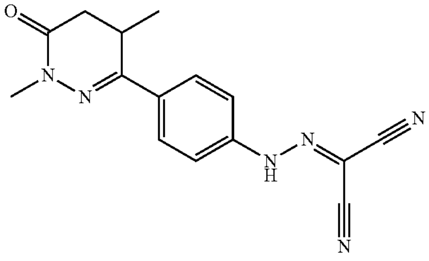 [SMILES: CC1CC(=O)N(C)N=C1c1ccc(NN=C(C#N)C#N)cc1]
12
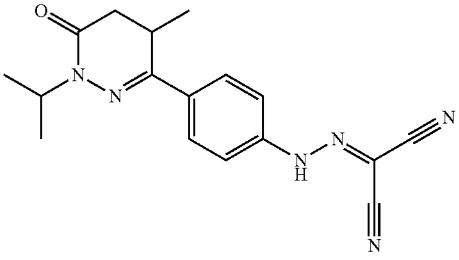 [SMILES: CC1CC(=O)N(C(C)C)N=C1c1ccc(NN=C(C#N)C#N)cc1]
13
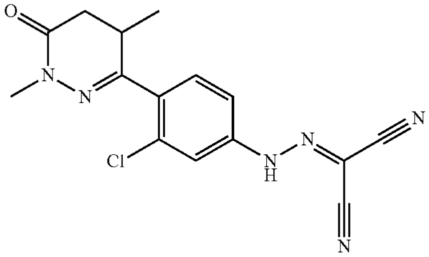 [SMILES: CC1CC(=O)N(C)N=C1c1ccc(NN=C(C#N)C#N)cc1Cl]

TABLE 1-continued

| | |
|---|---|
| 14 | 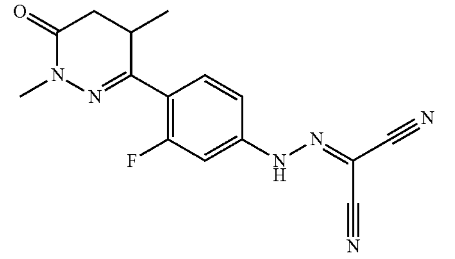 [SMILES: CC1CC(=O)N(C)N=C1c1ccc(NN=C(C#N)C#N)cc1F] |

Meanwhile, the compound of the present invention may exist in the form of a pharmaceutically acceptable salt. As the salt, an acid salt formed by a pharmaceutically acceptable free acid is useful. As used herein, the term "pharmaceutically acceptable salt" refers to any organic or inorganic addition salt of the compound represented by Formula 1 which is relatively non-toxic and harmless to patients, and side effects caused by this salt do not compromise the beneficial effects of this compound.

An acid addition salt is prepared by a conventional method, for example, by dissolving a compound in an excess amount of an aqueous acid solution and precipitating this solution using a water-miscible organic solvent such as methanol, ethanol, acetone, or acetonitrile. The same molar amounts of the compound and acid or alcohol (for example, glycol monoethyl ether) in water are heated, and subsequently the mixture may be evaporated and dried, or the precipitated salt may be suction-filtered.

In this case, as the free acid, an organic acid or an inorganic acid may be used. As the inorganic acid, hydrochloric acid, phosphoric acid, sulfuric acid, nitric acid, tartaric acid, or the like may be used. As the organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbon acid, vanillic acid, hydroiodic acid, or the like may be used. However, the present invention is not limited thereto.

Further, a pharmaceutically acceptable metal salt may be made using a base. An alkali metal salt or alkaline earth metal salt is obtained by dissolving the compound in an excess amount of an alkali metal hydroxide or alkaline earth metal hydroxide solution, filtering a non-soluble compound salt, and then evaporating and drying the filtrate. In this case, it is suitable for pharmaceutical use to prepare a sodium, potassium, or calcium salt as the metal salt, but the present invention is not limited thereto. Further, the corresponding silver salt may be obtained by reacting an alkali metal or alkaline earth metal salt with a suitable silver salt (for example, silver nitrate).

Pharmaceutically acceptable salts of the compounds of the present invention include salts of acidic or basic groups that may be present in the compounds of Formulae 1 to 3, unless otherwise indicated. For example, pharmaceutically acceptable salts may include sodium, calcium, and potassium salts of hydroxy groups, and other pharmaceutically acceptable salts of amino groups may include hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate). These pharmaceutically acceptable salts may be prepared using preparation methods of salts known in the art.

As the salts of the compounds of Formulae 1 to 3 of the present invention, any salt, as a pharmaceutically acceptable salt, may be used without limitation as long as it exhibits pharmacological activity equivalent to the compound of Formula 1, for example, it inhibits the aggregation and/or hyperphosphorylation of tau protein.

Further, the compounds represented by Formulae 1 to 3 according to the present invention include, without limitation, pharmaceutically acceptable salts thereof, as well as solvates such as possible hydrates that may be prepared therefrom, and all possible stereoisomers. The solvates and stereoisomers of the compounds represented by Formulae 1 to 3 may be prepared from the compounds represented by Formulae 1 to 3 using any method known in the art.

Moreover, the compounds represented by Formulae 1 to 3 according to the present invention may be prepared in a crystalline or amorphous form, and may be optionally hydrated or solvated if prepared in a crystalline form. In the present invention, compounds containing various amounts of water as well as stoichiometric hydrates of the compounds represented by Formulae 1 to 3 may be provided. The solvates of the compounds represented by Formulae 1 to 3 according to the present invention include both stoichiometric solvates and non-stoichiometric solvates.

A second aspect of the present invention provides a method of preparing the compound of Formula 1.

For example, the compound of the present invention may be prepared by way of a process including a step of reacting a compound represented by Formula 4 below including a reactive amine group at one end thereof with sodium nitrite and malononitrile in the presence of an acid to form an imine bond:

[Formula 4]

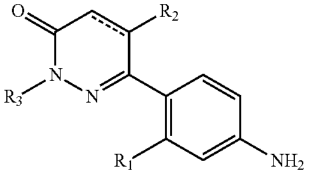

In Formula 4 above, $R_1$ to $R_3$ are as defined above.

Specifically, the process may be performed via a series of steps including:

- a first step of dissolving the compound of Formula 4 and sodium nitrite in a $C_{1-4}$ lower alcohol solvent and adding an aqueous acid solution thereto at a temperature of −5° C. to 5° C. to form a diazonium salt,
- a second step of adding malononitrile to the reaction solution including the diazonium salt obtained in the first step and performing a reaction at a temperature of 15° C. to 40° C., and
- a third step of adding an aqueous base solution to the reaction solution of the second step for neutralization. However, the present invention is not limited thereto.

Specifically, the compound of Formula 4 above used to prepare the compound of the present invention may be a compound represented by Formula 4-a or 4-b below:

[Formula 4-a]

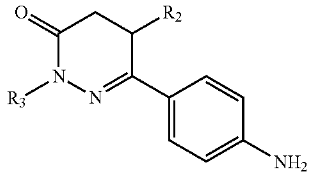

[Formula 4-b]

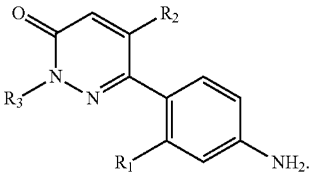

More specifically, the compound represented by Formula 4-a may be prepared by way of a series of processes including the steps of a-1) reacting 4-(4-acetamidophenyl-4-oxo-(unsubstituted or $R_2$-substituted)-butanoic acid with hydrazine, a-2) reacting N-(6-oxo-(unsubstituted or $R_2$-substituted)-1,4,5,6-tetrahydropyridazin-3-yl)phenyl)acetamide obtained in the previous step with an acid, and a-3) reacting 6-(4-aminophenyl-(unsubstituted or $R_2$-substituted)-4,5-dihydropyridazin-3(2H)-one obtained in the previous step with $R_3X$ (where X is halogen) under basic conditions optionally when $R_3$ is a substituent other than hydrogen, or step a-1') reacting 4-(4-aminophenyl)-4-oxo-(unsubstituted or $R_2$-substituted)-butanoic acid with unsubstituted or $R_3$-substituted hydrazine, without being limited thereto.

For example, as the compound represented by Formula 4-a, commercially available compounds may be used as purchased or may be synthesized using a reactant or intermediate of each step via reactions well known in the art alone or in combination, without being limited thereto.

In addition, if required, a process of isolating and/or purifying a product may further be performed using various methods well known in the art after each reaction.

For example, the reaction of step a-1) may be performed using a $C_{1-4}$ lower alcohol, e.g., ethanol or propanol, as a solvent, at a temperature of 70° C. to 130° C. for 1 hour to 12 hours, but is not limited thereto.

Also, the reaction of step a-2) may be performed in an aqueous solution phase containing water in a solvent at a temperature of 90° C. to 130° C. for 30 minutes to 6 hours and may further include a neutralization process by addition of a base, but is not limited thereto.

Furthermore, the reaction of step a-3) may be performed using NaH or $K_2CO_3$, as a base, and an organic solvent, such as dimethylformamide (DMF) or methylpyrrolidone (NMP), as a solvent, without being limited thereto. For example, the reaction may be performed at a low temperature around 0° C. for 5 hours to 24 hours while stirring, without being limited thereto.

Meanwhile, the reaction of step a-1') may be performed using a 01-4 lower alcohol, such as propanol, as an organic solvent, at a temperature of 80° C. to 120° C. in a microwave for 30 minutes to 6 hours while stirring, without being limited thereto.

More specifically, the compound represented by Formula 4-b above may be prepared by way of a series of processes including the steps of b-1) reacting by dissolving 3,6-dihalo(unsubstituted or $R_2$-substituted)pyridazine in an acid, and solidifying by adding a base thereto, b-2) reacting 6-halo-(unsubstituted or $R_2$-substituted) pyridazine-3(2H)-one prepared in the previous step with $R_3X$ (where X is halogen) under basic conditions optionally when $R_3$ is a substituent other than hydrogen, b-3) reacting 6-halo-2-(unsubstituted or $R_3$-substituted)-(unsubstituted or $R_2$-substituted)pyridazine-3(2H)-one obtained in the previous step with 4-amino or nitro-(unsubstituted or $R_1$-substituted phenyl)boronic acid pinacol ester in the presence of a $Pd(PPh_3)_2$ catalyst, and b-4) reacting the compound having a nitro substituent at one end thereof obtained in the previous step in the presence of a Pd/C catalyst under a hydrogen atmosphere to reduce the nitro group to an amine group, optionally, when the reaction is performed with 4-nitro-(unsubstituted or $R_1$-substituted phenyl)boronic acid pinacol ester in step b-3. However, the present invention is not limited thereto.

For example, as the compound represented by Formula 4-b, commercially available compounds may be used as purchased or may be synthesized using a reactant or intermediate of each step via reactions well known in the art alone or in combination, without being limited thereto.

In addition, if required, a process of isolating and/or purifying a product may further be performed after each reaction using various methods well known in the art.

For example, the reaction of step b-1) may be performed in an acid solution at a temperature of 100° C. to 115° C. while stirring for 6 hours to 24 hours, and then by adding a base in the form of an aqueous solution thereto and stirring the mixture at room temperature, without being limited thereto. In this case, the acid may be acetic acid or hydrochloric acid, without being limited thereto. Meanwhile, the base may be sodium hydrogen carbonate, potassium acetate, or sodium hydroxide, but is not limited thereto, and the type of the base is not particularly limited, as long as the base neutralizes to obtain a neutralized product.

Also, the reaction of step b-2) may be performed in an organic solvent, e.g., in a solution dissolved in DMF using potassium carbonate as a base at room temperature for 30 minutes to 10 hours while stirring, without being limited thereto.

In addition, the reaction of step b-3) above may be performed using an organic solvent, e.g., 1,4-dioxane, in the presence of an aqueous potassium phosphate solution by heating to 130° C. to 180° C. for 10 minutes to 5 hours in a microwave while stirring, without being limited thereto. For example, the reaction may be performed at a low temperature around 0° C. for 5 hours to 24 hours while stirring, without being limited thereto.

Furthermore, the reaction of step b-4) may be performed in an organic solvent, e.g., a 1,4-dioxane solution, without being limited thereto.

A third aspect of the present invention is to provide a composition for inhibiting aggregation of tau protein including the compound of the present invention as an active ingredient.

A fourth aspect of the present invention is to provide a composition for inhibiting hyperphosphorylation of tau protein including the compound of the present invention as an active ingredient.

A fifth aspect of the present invention is to provide a pharmaceutical composition for preventing or treating a disease caused by aggregation or hyperphosphorylation of tau protein including the compound of the present invention as an active ingredient.

In specific embodiments of the present invention, a total of 14 compounds, numbered 1 to 14 and represented by Formula 1, were newly synthesized, and the effects thereof on inhibiting aggregation and hyperphosphorylation of tau protein were confirmed. Moreover, in order to confirm the possibility of use as a pharmaceutical composition, it was confirmed that these compounds do not exhibit toxicity to cells.

As used herein, the term "prevention" refers to any action that inhibits or delays the occurrence, spread, and recurrence of a disease induced by aggregation or hyperphosphorylation of tau protein by administration of the pharmaceutical composition of the present invention, and the term "treatment" refers to any action in which symptoms of the disease are improved or beneficially changed by administration of the pharmaceutical composition of the present invention.

As described above, since the compound of the present invention not only inhibits aggregation or hyperphosphorylation of tau protein, but also does not exhibit toxicity to cells, the pharmaceutical composition containing this compound as an active ingredient may be used for the prevention or treatment of diseases caused by aggregation or hyperphosphorylation of tau protein. The disease caused by aggregation or hyperphosphorylation of tau protein to which the pharmaceutical composition of the present invention may be applied may be Alzheimer's disease, Parkinson's disease, vascular dementia, acute stroke, trauma, cerebrovascular disease, brain cord trauma, spinal cord trauma, peripheral neuropathy, retinopathy, glaucoma, or tauopathy. Non-limiting examples of the tauopathy may include chronic traumatic encephalopathy (CTE), primary age-related tauopathy, progressive supranuclear palsy, corticobasal degeneration, Pick's disease, argyrophilic grain disease (AGD), frontotemporal dementia (FTD), Parkinsonism linked to chromosome 17, Lytico-bodig disease (Parkinsonism-dementia complex of Guam), ganglioglioma, gangliocytoma, meningioangiomatosis, postencephalitic Parkinsonism, subacute sclerosing panencephalitis, lead encephalopathy, tuberous sclerosis, pantothenate kinase-associated neurodegeneration, lipofuscinosis, and traumatic brain injury.

For example, the composition of the present invention may further include a pharmaceutically acceptable carrier, a diluent, or an excipient, may be formulated and used in various forms such as oral formulations such as powders, granules, tablets, capsules, suspensions, emulsions, syrups, aerosols, and injection drugs of sterile injection solutions according to a general method for each purpose of use, and may be administered orally or may be administered through various routes including intravenous, intraperitoneal, subcutaneous, rectal, and topical administrations. Examples of the suitable carrier, excipient, or diluent included in this composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil. The composition of the present invention may further include a filler, an anti-aggregating agent, a lubricant, a humectant, a flavoring agent, an emulsifying agent, a preservative, and the like.

Solid preparations for oral administration include tablets, pills, powders, granules, capsules, and the like, and such a solid preparation is formulated by mixing one or more excipients, such as starch, calcium carbonate, sucrose, lactose, and gelatin with the composition. Meanwhile, in addition to a simple excipient, a lubricant such as magnesium stearate or talc may be used.

As the oral liquid formulation, a suspension, a solution for internal use, an emulsion, a syrup, and the like may be exemplified, and the oral liquid formulation may include various excipients, such as a humectant, a sweetening agent, a fragrance, and a preservative in addition to water and liquid paraffin, which are commonly used as a simple diluent.

Preparations for parenteral administration include an aqueous solvent, a non-aqueous solvent, a suspension agent, an emulsifying agent, a lyophilized preparation, and a suppository, which are sterilized.

As the non-aqueous solvent or the suspension agent, propylene glycol, polyethylene glycol, plant oil such as olive oil, injectable ester such as ethyloleate, or the like may be used. As a base of the suppository, witepsol, macrogol, twin 61, cacao oil, laurin oil, glycerogelatin, or the like may be used. Meanwhile, injectables may include conventional additives such as a solubilizing agent, an isotonic agent, a suspension agent, an emulsifying agent, a stabilizing agent, and a preservative.

The formulation may be prepared using a conventional mixing, granulating, or coating method, and may contain an active ingredient in an amount of about 0.1 wt % to 75 wt %, preferably about 0.1 wt % to 50 wt %. The unit formulation for a mammal weighing about 50 kg to 70 kg contains about 10 mg to 200 mg of an active ingredient.

In this case, the composition of the present invention is administered in a pharmaceutically effective amount. As used herein, the term "pharmaceutically effective amount" refers to an amount sufficient to treat a disease at a reasonable benefit/risk ratio applicable to medical treatment and not cause side effects, and the level of the effective amount may be determined depending on patient's health status, type of disease, severity, activity of a drug, sensitivity to a drug, administration method, administration time, administration route, excretion rate, treatment period, factors including drugs used in combination or concurrently, and other factors well known in the medical field. The composition of the present invention may be administered as an individual therapeutic agent or administered in combination with other therapeutic agents, may be administered sequentially or simultaneously with a conventional therapeutic agent, and may be administered in a single dose or multiple doses. It is important to administer a minimum amount capable of obtaining the maximum effect without side effects in consideration of all of the above factors, which may be easily determined by those skilled in the art.

For example, since a dosage may increase or decrease depending on administration route, disease severity, sex, weight, age, and the like, the dosage does not limit the scope of the present invention in any way.

A preferred dosage of the compound of the present invention varies depending on the condition and weight of a patient, severity of disease, the form of drug, and the route and duration of administration, but may be appropriately selected by those skilled in the art. However, for a desired effect, the compound of the present invention may be administered in an amount of 0.0001 mg/kg to 100 mg/kg (body weight), preferably 0.001 mg/kg to 100 mg/kg (body weight) per day. The compound may be administered once a day or several times a day in divided doses via an oral or parenteral route.

A sixth aspect of the present invention is to provide a method for preventing or treating a disease caused by aggregation or hyperphosphorylation of tau protein, the method including administering the pharmaceutical composition of the present invention to a subject in need thereof.

As used herein, the term "subject" refers to any animal including monkeys, cows, horses, sheep, pigs, chickens, turkeys, quails, cats, dogs, mice, rabbits, and guinea pigs in addition to humans, which have developed or may develop a disease caused by aggregation or hyperphosphorylation of tau protein. The diseases may be effectively prevented or treated by administration of the pharmaceutical composition of the present invention to the subject. Further, since the pharmaceutical composition of the present invention exhibits a therapeutic effect by inhibiting aggregation or hyperphosphorylation of tau protein, a synergistic effect may be exhibited by administering this composition in combination with a conventional therapeutic agent.

As used herein, the term "administration" refers to providing a predetermined substance to a patient using any suitable method, and the administration route of the composition of the present invention may be any general route as long as the substance is able to reach target tissue. The composition may be administered through intraperitoneal administration, intravenous administration, intramuscular administration, subcutaneous administration, intradermal administration, oral administration, topical administration, intranasal administration, intrapulmonary administration, or rectal administration, but the present invention is not limited thereto. Also, the pharmaceutical composition of the present invention may be administered using any device capable of moving an active substance to a target cell. Preferred administrations and formulations include intravenous injection drugs, subcutaneous injection drugs, intradermal injection drugs, intramuscular injection drugs, and dropwise injection drugs. The injection drugs may be prepared using an aqueous solvent such as a physiological saline solution or Ringer's solution, or a non-aqueous solvent such as plant oil, a higher fatty acid ester (for example, ethyl oleate), or an alcohol (for example, ethanol, benzyl alcohol, propylene glycol, or glycerin), and may include a pharmaceutical carrier such as a stabilizing agent for preventing denaturing (for example, ascorbic acid, sodium hydrogen sulfite, sodium pyrosulfite, BHA, tocopherol, or EDTA), an emulsifying agent, a buffering agent for pH control, or a preservative for inhibiting the growth of microorganisms (for example, phenylmercury nitrate, thimerosal, benzalkonium chloride, phenol, cresol, or benzyl alcohol).

BEST MODE

Hereinafter, the present invention will be described in more detail with reference to examples and experimental examples. However, these examples and experimental examples are only illustrative of the present invention, and the scope of the present invention is not limited to these examples and experimental examples.

Example 1: Preparation of (4-(1-isopropyl-6-oxo-1,4,5,6-tetrahydropyridazin-3-yl)phenyl)carbonohydrazonoyl dicyanide (Compound 1)

Step 1-1: Preparation of 6-(4-aminophenyl)-2-isopropyl-4,5-dihydropyridazin-3(2H)-one 6-(4-Aminophenyl)-4,5-dihydropyridazin-3(2H)-one (105 mg, 0.55 mmol) and 60% sodium hydride (24 mg, 0.61 mmol) were dissolved in dimethylformamide (DMF), and 2-iodopropane (58 μL, 0.58 mmol) was added thereto, followed by stirring at 0° C. for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 121 mg (yield: 99%) of the title compound.

$^1$H NMR (400 MHz, DMSO-$d_6$) δ7.51 (d, J=8.6 Hz, 2H), 6.58 (d, J=8.7 Hz, 2H), 5.51 (s, 2H), 4.84 (p, J=6.6 Hz, 1H), 2.79 (dd, J=8.9 Hz, 7.3 Hz, 2H), 2.39 (dd, J=8.9 Hz, 7.2 Hz, 2H), 1.17 (d, J=6.6 Hz, 6H).

Step 1-2: Preparation of (4-(1-isopropyl-6-oxo-1,4,5,6-tetrahydropyridazin-3-yl)phenyl)carbonohydrazonoyl dicyanide 6-(4-Aminophenyl)-2-isopropyl-4,5-dihydropyridazin-3(2H)-one (110 mg, 0.47 mmol) obtained in step 1-1 above and sodium nitrite (15 mg, 0.23 mmol) were dissolved in ethanol in the presence of nitrogen, and a 1.0 M aqueous hydrochloric acid solution (0.3 mL, 0.30 mmol) was added thereto at 0° C. The reaction mixture was stirred at 0° C. for 10 minutes to form a diazonium salt. Malononitrile (19 mg, 0.28 mmol) was added to the reaction mixture including the diazonium salt, and the mixture was stirred at room temperature for 10 minutes. Thereafter, the pH of the reaction mixture was adjusted to 6.0 using an aqueous sodium hydroxide solution, and the reaction mixture was further stirred at room temperature for 1 hour. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 140 mg (yield: 95%) of the title compound.

$^1$H NMR (400 MHz, DMSO-$d_6$) δ13.11 (5, 1H), 7.87 (d, J=8.9 Hz, 2H), 7.53 (d, J=8.9 Hz, 2H), 4.88 (p, J=6.6 Hz, 1H), 2.92 (dd, J=8.9 Hz, 7.5 Hz, 2H), 2.49 (m, 2H), 1.20 (d, J=6.7 Hz, 6H).

Example 2: Preparation of (4-(1-isopropyl-4-methyl-6-oxo-1,4,5,6-tetrahydropyridazin-3-yl)phenyl)carbonohydrazonoyl dicyanide (Compound 2)

Step 2-1: Preparation of 6-(4-aminophenyl)-2-isopropyl-5-methyl-4,5-dihydropyridazin-3(2H)-one 194 mg (yield: 75%) of the title compound was obtained in the same manner as in step 1-1 of Example 1, except that 6-(4-aminophenyl)-5-methyl-4,5-dihydropyridazin-3(2H)-one (200 mg, 0.98 mmol) was used instead of 6-(4-aminophenyl)-4,5-dihydropyridazin-3(2H)-one.

$^1$H NMR (400 MHz, DMSO-$d_6$) δ7.53 (d, J=8.7 Hz, 2H), 6.59 (d, J=8.7 Hz, 2H), 5.53 (s, 2H), 4.88 (p, J=6.7 Hz, 1H), 3.31-3.19 (m, 1H), 2.59 (dd, J=16.5 Hz, 6.6 Hz, 1H), 2.23 (dd, J=16.5 Hz, 1.6 Hz, 1H), 1.22 (d, J=6.6 Hz, 3H), 1.12 (d, J=6.7 Hz, 3H), 1.00 (d, J=7.3 Hz, 3H).

Step 2-2: Preparation of (4-(1-isopropyl-4-methyl-6-oxo-1,4,5,6-tetrahydropyridazin-3-yl)phenyl)carbonohydrazonoyl dicyanide 229 mg (yield: 97%) of the title compound was obtained in the same manner as in step 1-2 of Example 1, except that 6-(4-aminophenyl)-2-isopropyl-5-methyl-4,5-dihydropyridazin-3(2H)-one (180 mg, 0.73 mmol) obtained in step 2-1 above was used instead of 6-(4-aminophenyl)-2-isopropyl-4,5-dihydropyridazin-3(2H)-one.

$^1$H NMR (400 MHz, DMSO-$d_6$) δ13.14 (s, 1H), 7.90 (d, J=8.8 Hz, 2H), 7.54 (d, J=8.8 Hz, 2H), 4.91 (p, J=6.6 Hz, 1H), 2.71 (dd, J=16.6 Hz, 6.8 Hz, 1H), 2.32 (dd, J=16.6, 1.5 Hz, 1H), 1.25 (d, J=6.6 Hz, 3H), 1.16 (d, J=6.7 Hz, 3H), 1.04 (d, J=7.2 Hz, 3H).

Example 3: Preparation of (4-(1-ethyl-4-methyl-6-oxo-1,4,5,6-tetrahydropyridazin-3-yl)phenyl)carbonohydrazonoyl dicyanide (Compound 3)

Step 3-1: Preparation of 6-(4-aminophenyl)-2-ethyl-5-methyl-4,5-dihydropyridazin-3(2H)-one 79 mg (yield: 65%) of the title compound was obtained in the same manner as in step 1-1 of Example 1, except that 6-(4-aminophenyl)-5-methyl-4,5-dihydropyridazin-3(2H)-one (100 mg, 0.53 mmol) was used instead of 6-(4-aminophenyl)-4,5-dihydropyridazin-3(2H)-one and 2-iodoethane (47 μL, 0.58 mmol) was used instead of iodopropane.

$^1$H NMR (400 MHz, DMSO-$d_6$) δ7.51 (d, J=8.6 Hz, 2H), 6.58 (d, J=8.7 Hz, 2H), 5.53 (s, 2H), 3.73 (ddq, J=51.9 Hz, 13.8 Hz, 7.1 Hz, 2H), 3.30-3.24 (m, 1H), 2.89 (s, 1H), 2.73 (s, 1H), 2.61 (dd, J=16.5 Hz, 6.6 Hz, 1H), 2.23 (d, J=16.6 Hz, 1H), 1.13 (t, J=7.1 Hz, 3H), 1.02 (d, J=7.3 Hz, 3H).

Step 3-2: Preparation of (4-(1-ethyl-4-methyl-6-oxo-1,4,5,6-tetrahydropyridazin-3-yl)phenyl)carbonohydrazonoyl dicyanide 33 mg (yield: 35%) of the title compound was obtained in the same manner as in step 1-2 of Example 1, except that 6-(4-aminophenyl)-2-ethyl-5-methyl-4,5-dihydropyridazin-3(2H)-one (70 mg, 0.30 mmol) obtained in step 3-1 above was used instead of 6-(4-aminophenyl)-2-isopropyl-4,5-dihydropyridazin-3(2H)-one.

$^1$H NMR (400 MHz, DMSO-$d_6$) δ13.13 (s, 1H), 7.88 (d, J=8.9 Hz, 2H), 7.53 (d, J=8.8 Hz, 2H), 3.79 (ddt, J=32.0 Hz, 13.5 Hz, 6.8 Hz, 2H), 2.73 (dd, J=16.6 Hz, 6.7 Hz, 1H), 2.35-2.23 (m, 1H), 1.16 (t, J=7.1 Hz, 3H), 1.07 (d, J=7.2 Hz, 3H).

Example 4: Preparation of (4-(4-methyl-6-oxo-1-(2,2,2-trifluoroethyl)-1,4,5,6-tetrahydropyridazin-3-yl)phenyl)carbonohydrazonoyl dicyanide (Compound 4)

Step 4-1: Preparation of 6-(4-aminophenyl)-5-methyl-2-(2,2,2-trifluoroethyl)-4,5-dihydropyridazin-3(2H)-one 4-(4-Aminophenyl)-3-methyl-4-oxobutanoic acid hydrochloride (100 mg, 0.41 mmol) and 65% (2,2,2-trifluoroethyl)hydrazine (83 μL, 0.61 mmol) were dissolved in propanol, and the reaction mixture was stirred in a microwave at 100° C. for 3 hours. Upon completion of the reaction, a reaction product was extracted using distilled water and ethyl acetate to obtain an organic layer, and the organic layer was dried over anhydrous magnesium sulfate and filtered. Thereafter, the filtrate was concentrated under reduced pressure and purified by column chromatography to obtain 52 mg (yield: 45%) of the title compound.

$^1$H NMR (400 MHz, DMSO-$d_6$) δ7.52 (d, J=8.7 Hz, 2H), 6.59 (d, J=8.7 Hz, 2H), 5.61 (s, 2H), 4.81 (dq, J=15.1 Hz, 9.3 Hz, 1H), 4.25 (dq, J=15.1 Hz, 9.2 Hz, 1H), 3.41-3.35 (m, 1H), 2.75 (dd, J=16.7 Hz, 6.4 Hz, 1H), 2.38 (dd, J=16.7 Hz, 1.6 Hz, 1H), 1.04 (d, J=7.2 Hz, 3H).

Step 4-2: Preparation of (4-(4-methyl-6-oxo-1-(2,2,2-trifluoroethyl)-1,4,5,6-tetrahydropyridazin-3-yl)phenyl)carbonohydrazonoyl dicyanide 45 mg (yield: 70%) of the title compound was obtained in the same manner as in step 1-2 of Example 1, except that 6-(4-aminophenyl)-5-methyl-2-(2,2,2-trifluoroethyl)-4,5-dihydropyridazin-3(2H)-one (50 mg, 0.17 mmol) obtained in step 4-1 above was used instead of 6-(4-aminophenyl)-2-isopropyl-4,5-dihydropyridazin-3(2H)-one.

$^1$H NMR (400 MHz, DMSO-$d_6$) δ13.14 (s, 1H), 7.88 (d, J=8.9 Hz, 2H), 7.55 (d, J=8.9 Hz, 2H), 4.86 (dq, J=15.2 Hz, 9.3 Hz, 1H), 4.34 (dq, J=15.1 Hz, 9.1 Hz, 1H), 3.49 (td, J=7.1 Hz, 1.7 Hz, 1H), 2.86 (dd, J=16.8 Hz, 6.6 Hz, 1H), 2.49-2.44 (m, 1H), 1.09 (d, J=7.2 Hz, 3H).

Example 5: Preparation of (4-(1-(2-methoxyethyl)-4-methyl-6-oxo-1,4,5,6-tetrahydropyridazin-3-yl)phenyl)carbonohydrazonoyl dicyanide (Compound 5)

Step 5-1: Preparation of 6-(4-aminophenyl)-2-(2-methoxyethyl)-5-methyl-4,5-dihydropyridazin-3(2H)-one 84 mg (yield: 61%) of the title compound was obtained in the same manner as in step 1-1 of Example 1, except that 6-(4-aminophenyl)-5-methyl-4,5-dihydropyridazin-3(2H)-one (100 mg, 0.53 mmol) was used instead of 6-(4-aminophenyl)-4,5-dihydropyridazin-3(2H)-one, and 1-bromo-2-methoxyethane (55 μL, 0.58 mmol) was used instead of iodopropane.

$^1$H NMR (400 MHz, DMSO-$d_6$) δ7.52 (d, J=8.6 Hz, 2H), 6.58 (d, J=8.7 Hz, 2H), 5.56 (s, 2H), 4.11-4.05 (m, 1H), 3.74-3.63 (m, 1H), 3.58-3.49 (m, 2H), 3.29 (t, J=7.0 Hz, 1H), 3.24 (s, 3H), 2.63 (dd, J=16.5 Hz, 6.5 Hz, 1H), 2.25 (dd, J=16.5 Hz, 1.5 Hz, 1H), 1.03 (d, J=7.3 Hz, 3H).

Step 5-2: Preparation of (4-(1-(2-methoxyethyl)-4-methyl-6-oxo-1,4,5,6-tetrahydropyridazin-3-yl)phenyl)carbonohydrazonoyl dicyanide 35 mg (yield: 34%) of the title compound was obtained in the same manner as in step 1-2 of Example 1, except that 6-(4-aminophenyl)-2-(2-methoxyethyl)-5-methyl-4,5-dihydropyridazin-3(2H)-one (80 mg, 0.31 mmol) obtained in step 5-1 above was used instead of 6-(4-aminophenyl)-2-isopropyl-4,5-dihydropyridazin-3(2H)-one.

$^1$H NMR (400 MHz, DMSO-$d_6$) δ13.14 (s, 1H), 7.88 (d, J=8.6 Hz, 2H), 7.54 (d, J=8.5 Hz, 2H), 4.10 (dt, J=12.8 Hz, 6.0 Hz, 1H), 3.75 (dt, J=13.6 Hz, 5.6 Hz, 1H), 3.62-3.52 (m, 2H), 3.24 (5, 3H), 2.74 (dd, J=16.6 Hz, 6.7 Hz, 1H), 2.33 (d, J=16.6 Hz, 1H), 1.07 (d, J=7.2 Hz, 3H).

Example 6: Preparation of (4-(1-cyclopropyl-4-methyl-6-oxo-1,4,5,6-tetrahydropyridazin-3-yl)phenyl)carbonohydrazonoyl dicyanide (Compound 6)

Step 6-1: Preparation of 6-(4-aminophenyl)-2-cyclopropyl-5-methyl-4,5-dihydropyridazin-3(2H)-one 6-(4-Aminophenyl)-5-methyl-4,5-dihydropyridazin-3(2H)-one (100 mg, 0.53 mmol) and 60% sodium hydride (25 mg, 0.63 mmol) were dissolved in methylpyrrolidone (NMP), and bromocyclopropane (46 μL, 0.58 mmol) was added thereto, and then the reaction mixture was stirred in a microwave at 180° C. for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was solidified using ether to obtain 41 mg (yield: 30%) of the title compound.

$^1$H NMR (400 MHz, DMSO-$d_6$) δ7.48 (d, J=8.4 Hz, 2H), 6.57 (d, J=8.4 Hz, 2H), 5.54 (s, 2H), 3.50 (tt, J=7.5 Hz, 4.2 Hz, 1H), 3.26 (dd, J=7.9 Hz, 6.1 Hz, 1H), 2.63 (dd, J=16.6 Hz, 6.6 Hz, 1H), 2.26 (d, J=16.6 Hz, 1H), 0.98 (d, J=7.3 Hz, 3H), 0.92-0.82 (m, 1H), 0.79-0.68 (m, 3H).

Step 6-2: Preparation of (4-(1-cyclopropyl-4-methyl-6-oxo-1,4,5,6-tetrahydropyridazin-3-yl)phenyl)carbonohydrazonoyl dicyanide 36 mg (yield: 96%) of the title compound was obtained in the same manner as in step 1-2 of Example 1, except that 6-(4-aminophenyl)-2-cyclopropyl-5-methyl-4,5-dihydropyridazin-3(2H)-one (30 mg, 0.12 mmol) obtained in step 6-1 above was used instead of 6-(4-aminophenyl)-2-isopropyl-4,5-dihydropyridazin-3(2H)-one.

$^1$H NMR (400 MHz, DMSO-$d_6$) δ13.11 (s, 1H), 7.85 (d, J=8.5 Hz, 2H), 7.52 (d, J=8.5 Hz, 2H), 3.50 (p, J=6.4 Hz, 1H), 3.39-3.35 (m, 1H), 2.74 (dd, J=16.7 Hz, 6.8 Hz, 1H), 2.34 (d, J=16.6 Hz, 1H), 1.03 (d, J=7.2 Hz, 3H), 0.96-0.85 (m, 1H), 0.83-0.70 (m, 3H).

Example 7: Preparation of (4-(1-(4-methoxyphenyl)-4-methyl-6-oxo-1,4,5,6-tetrahydropyridazin-3-yl)phenyl)carbonohydrazonoyl dicyanide (Compound 7)

Step 7-1: Preparation of 6-(4-aminophenyl)-2-(4-methoxyphenyl)-5-methyl-4,5-dihydropyridazin-3(2H)-one 34 mg (yield: 27%) of the title compound was obtained in the same manner as in step 4-1 of Example 4, except that (4-methoxyphenyl)hydrazine hydrochloride (107 mg, 0.61 mmol) was used instead of (2,2,2-trifluoroethyl)hydrazine.

$^1$H NMR (400 MHz, DMSO-$d_6$) δ7.54 (d, J=8.7 Hz, 2H), 7.39 (d, J=9.0 Hz, 2H), 6.96 (d, J=9.0 Hz, 2H), 6.58 (d, J=8.7 Hz, 2H), 5.58 (5, 2H), 3.78 (s, 3H), 3.46-3.37 (m, 1H), 2.86 (dd, J=16.5 Hz, 6.5 Hz, 1H), 2.40 (dd, J=16.5 Hz, 1.6 Hz, 1H), 1.15 (d, J=7.3 Hz, 3H).

Step 7-2: Preparation of (4-(1-(4-methoxyphenyl)-4-methyl-6-oxo-1,4,5,6-tetrahydropyridazin-3-yl)phenyl)carbonohydrazonoyl dicyanide 29 mg (yield: 77%) of the title compound was obtained in the same manner as in step 1-2 of Example 1, except that 6-(4-aminophenyl)-2-(4-methoxyphenyl)-5-methyl-4,5-dihydropyridazin-3(2H)-one (30 mg, 0.29 mmol) obtained in step 7-1 above was used instead of 6-(4-aminophenyl)-2-isopropyl-4,5-dihydropyridazin-3(2H)-one.

$^1$H NMR (400 MHz, DMSO-$d_6$) δ13.15 (s, 1H), 7.90 (d, J=8.9 Hz, 2H), 7.54 (d, J=8.8 Hz, 2H), 7.39 (d, J=8.9 Hz, 2H), 6.98 (d, J=9.0 Hz, 2H), 3.79 (s, 3H), 3.59-3.46 (m, 1H), 2.97 (dd, J=16.6 Hz, 6.6 Hz, 1H), 2.45 (5, 1H), 1.20 (d, J=7.3 Hz, 3H).

Example 8: Preparation of (4-(1-methyl-6-oxo-1,6-dihydropyridazin-3-yl)phenyl)carbonohydrazonoyl dicyanide (Compound 8)

Step 8-1: Preparation of 6-chloropyridazine-3(2H)-one 3,6-Dichloropyridazine (1 g, 6.71 mmol) was dissolved in acetic acid (26 mL), and the reaction mixture was stirred at 110° C. for 12 hours. Upon completion of the reaction, the reaction mixture was concentrated, an aqueous sodium hydrogen carbonate solution was added thereto, and the mixture was stirred at room temperature to solidify the reactant. The resultant was concentrated under reduced pressure to obtain 420 mg (yield: 48%) of the title compound.

$^1$H NMR (400 MHz, DMSO-$d_6$) δ13.18 (s, 1H), 7.52 (d, J=9.8 Hz, 1H), 6.98 (d, J=9.9 Hz, 1H).

Step 8-2: Preparation of 6-chloro-2-methylpyridazine-3(2H)-one

6-Chloropyridazine-3(2H)-one (100 mg, 0.77 mmol) obtained in step 8-1 of Example 8 above, iodomethane (95 μL, 1.53 mmol), and potassium carbonate (212 mg, 1.53 mmol) were dissolved in DMF, and the reaction mixture was stirred at room temperature for 4 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 82 mg (yield: 74%) of the title compound.

$^1$H NMR (400 MHz, DMSO-$d_6$) δ13.05 (s, 1H), 7.45 (d, J=1.3 Hz, 1H), 2.06 (d, J=1.4 Hz, 3H).

Step 8-3: Preparation of 6-(4-aminophenyl-2-methylpyridazine-3(2H)-one

6-Chloro-2-methylpyridazine-3(2H)-one (65 mg, 0.45 mmol) obtained in step 8-2 of Example 8 above and 4-aminophenylboronic acid pinacol ester (98 mg, 0.45 mmol) were dissolved in a 1,4-dioxane solution, and $Pd(PPh_3)_2$ (52 mg, 0.04 mmol) and a 2.0 M aqueous potassium phosphate solution (0.9 mL, 1.80 mmol) were added thereto. The reaction mixture was stirred at 160° C. for 1.5 hours in a microwave. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 86 mg (yield: 95%) of the title compound.

$^1$H NMR (400 MHz, DMSO-$d_6$) δ7.90 (d, J=9.7 Hz, 1H), 7.57 (d, J=8.5 Hz, 2H), 6.94 (d, J=9.7 Hz, 1H), 6.62 (d, J=8.6 Hz, 2H), 5.50 (s, 2H), 3.68 (s, 3H).

Step 8-4: Preparation of (4-(1-methyl-6-oxo-1,6-dihydropyridazin-3-yl)phenyl)carbonohydrazonoyl dicyanide 41 mg (yield: 59%) of the title compound was obtained in the same manner as in step 1-2 of Example 1, except that 6-(4-aminophenyl)-2-methylpyridazine-3(2H)-one (50 mg, 0.25 mmol) obtained in step 8-3 above was used instead of 6-(4-aminophenyl)-2-isopropyl-4,5-dihydropyridazin-3 (2H)-one.

$^1$H NMR (400 MHz, DMSO-$d_6$) δ13.14 (5, 1H), 8.06 (d, J=9.8 Hz, 1H), 7.95 (d, J=8.9 Hz, 2H), 7.57 (d, J=8.8 Hz, 2H), 7.05 (d, J=9.7 Hz, 1H), 3.74 (s, 3H).

Example 9: Preparation of (4-(1-isopropyl-6-oxo-1,6-dihydropyridazin-3-yl)phenyl)carbonohydrazonoyl dicyanide (Compound 9)

Step 9-1: Preparation of 6-chloro-2-isopropylpyridazine-3(2H)-one 107 mg (yield: 81%) of the title compound was obtained in the same manner as in step 8-2 of Example 8 above, except that 2-iodopropane (153 μL, 1.53 mmol) was used instead of iodomethane.

$^1$H NMR (400 MHz, Chloroform-d) δ7.14 (d, J=9.6 Hz, 1H), 6.89 (d, J=9.6 Hz, 1H), 5.23 (pd, J=6.7 Hz, 0.8 Hz, 1H), 1.36 (dd, J=6.6 Hz, 0.9 Hz, 6H).

Step 9-2: Preparation of 6-(4-aminophenyl)-2-isopropylpyridazine-3(2H)-one 77 mg (yield: 58%) of the title compound was obtained in the same manner as step 8-3 of Example 8 above, except that 6-chloro-2-isopropylpyridazine-3(2H)-one (100 mg, 0.58 mmol) obtained in step 9-1 above was used instead of 6-chloro-2-methylpyridazine-3(2H)-one.

$^1$H NMR (400 MHz, DMSO-$d_6$) δ7.86 (d, J=10.0 Hz, 1H), 7.61 (d, J=3.6 Hz, 2H), 6.90 (d, J=10.2 Hz, 1H), 6.64 (d, J=3.8 Hz, 2H), 5.49 (s, 2H), 5.18 (q, J=6.4 Hz, 1H), 1.33 (s, 6H).

Step 9-3: Preparation of (4-(1-isopropyl-6-oxo-1,6-dihydropyridazin-3-yl)phenyl)carbonohydrazonoyl dicyanide 74 mg (yield: 92%) of the title compound was obtained in the same manner as step 1-2 of Example 1 above, except that 6-(4-aminophenyl)-2-isopropylpyridazine-3(2H)-one (60 mg, 0.26 mmol) obtained in step 9-2 above was used instead of 6-(4-aminophenyl)-2-isopropyl-4,5-dihydropyridazin-3 (2H)-one.

$^1$H NMR (400 MHz, DMSO-$d_6$) δ13.14 (s, 1H), 8.03 (d, J=9.8 Hz, 1H), 7.99 (d, J=8.9 Hz, 2H), 7.57 (d, J=8.9 Hz, 2H), 7.02 (d, J=9.7 Hz, 1H), 5.21 (p, J=6.6 Hz, 1H), 1.35 (d, J=6.7 Hz, 6H).

Example 10: Preparation of (4-(1-(difluoromethyl)-6-oxo-1,6-dihydropyridazin-3-yl)phenyl)carbonohydrazonoyl dicyanide (Compound 10)

Step 10-1: Preparation of 6-chloro-2-(difluoromethyl)pyridazine-3(2H)-one and 3-chloro-6-(difluoromethoxy)pyridazine A mixture of the title compounds was obtained in the same manner as in step 8-2 of Example 8 above, except that sodium 2-chloro-2,2-difluoroacetate (234 mg, 1.53 mmol) was used instead of iodomethane, and a solvent was removed therefrom to use the title compounds in the next step without additional purification.

Step 10-2: Preparation of 6-(4-aminophenyl)-2-(difluoromethyl)pyridazine-3(2H)-one and 4-(6-(difluoromethoxy)pyridazine-3-yl)aniline 35 mg (yield: 27%) of 6-(4-aminophenyl)-2-(difluoromethyl)pyridazine-3(2H)-one and 41 mg (yield: 31%) of 4-(6-(difluoromethoxy)pyridazine-3-yl)aniline, as the title compounds, were obtained in the same manner as in step 8-3 of Example 8, except that the mixture of 6-chloro-2-(difluoromethyl)pyridazine-3(2H)-one and 3-chloro-6-(difluoromethoxy)pyridazine (100 mg, 0.55 mmol) obtained in step 10-1 above was used instead of 6-chloro-2-methylpyridazine-3(2H)-one.

6-(4-Aminophenyl)-2-(difluoromethyl)pyridazine-3 (2H)-one $^1$H NMR (400 MHz, DMSO-$d_6$) δ8.06 (d, J=10.2 Hz, 1H), 7.93 (t, J=60.0 Hz, 1H), 7.63 (d, J=8.6 Hz, 2H), 7.07 (d, J=9.9 Hz, 1H), 6.65 (d, J=8.7 Hz, 2H), 5.68 (s, 2H); and 4-(6-(difluoromethoxy)pyridazine-3-yl)aniline $^1$H NMR (400 MHz, DMSO-$d_6$) δ8.19 (d, J=9.3 Hz, 1H), 7.89 (t, J=72.1 Hz, 1H), 7.82 (d, J=8.6 Hz, 2H), 7.47 (d, J=9.3 Hz, 1H), 6.67 (d, J=8.6 Hz, 2H), 5.61 (s, 2H).

Step 10-3: Preparation of (4-(1-(difluoromethyl)-6-oxo-1,6-dihydropyridazin-3-yl)phenyl)carbonohydrazonoyl dicyanide 20 mg (yield: 59%) of the title compound was obtained in the same manner as in step 1-2 of Example 1 above, except that 6-(4-aminophenyl)-2-(difluoromethyl)pyridazine-3 (2H)-one (26 mg, 0.11 mmol) obtained in step 10-2 above was used instead of 6-(4-aminophenyl)-2-isopropyl-4,5-dihydropyridazin-3(2H)-one.

$^1$H NMR (400 MHz, DMSO-$d_6$) δ13.12 (s, 1H), 8.19 (d, J=10.0 Hz, 1H), 7.99 (d, J=8.8 Hz, 2H), 7.98 (t, J=58.2 Hz, 1H), 7.59 (d, J=8.8 Hz, 2H), 7.20 (d, J=10.0 Hz, 1H).

Example 11: Preparation of (4-(1,4-dimethyl-6-oxo-1,6-dihydropyridazin-3-yl)phenyl)carbonohydrazonoyl dicyanide (Compound 11)

Step 11-1: Preparation of 6-chloro-2,5-dimethylpyridazine-3(2H)-one 53 mg (yield: 49%) of the title compound was obtained in the same manner as in step 8-2 of Example 8, except that 6-chloro-5-methylpyridazine-3(2H)-one (100 mg, 0.69 mmol) was used instead of 6-chloropyridazine-3(2H)-one.

$^1$H NMR (400 MHz, DMSO-$d_6$) δ6.79 (d, J=1.3 Hz, 1H), 3.73 (s, 3H), 2.26 (d, J=1.3 Hz, 3H).

Step 11-2: Preparation of 6-(4-aminophenyl)-2,5-dimethylpyridazine-3(2H)-one 51 mg (yield: 76%) of the title compound was obtained in the same manner as in step 8-3 of Example 8 above, except that 6-chloro-2,5-dimethylpyridazine-3(2H)-one (50 mg, 0.31 mmol) obtained in step 11-1 above was used instead of 6-chloro-2-methylpyridazine-3(2H)-one.

$^1$H NMR (400 MHz, DMSO-$d_6$) δ7.82 (d, J=1.4 Hz, 1H), 7.56 (d, J=8.6 Hz, 2H), 6.61 (d, J=8.7 Hz, 2H), 5.47 (s, 2H), 3.68 (s, 3H), 2.13 (d, J=1.2 Hz, 3H).

Step 11-3: Preparation of (4-(1,4-dimethyl-6-oxo-1, 6-dihydropyridazin-3-yl)phenyl)carbonohydrazonoyl dicyanide 37 mg (yield: 77%) of the title compound was obtained in the same manner as in step 1-2 of Example 1 above, except that 6-(4-aminophenyl)-2,5-dimethylpyridazine-3(2H)-one (35 mg, 0.16 mmol) obtained in step 11-2 above was used instead of 6-(4-aminophenyl)-2-isopropyl-4,5-dihydropyridazin-3(2H)-one.

$^1$H NMR (400 MHz, DMSO-$d_6$) δ13.14 (5, 1H), 7.98 (s, 1H), 7.94 (d, J=8.8 Hz, 2H), 7.56 (d, J=8.9 Hz, 2H), 3.74 (s, 3H), 2.16 (d, J=1.2 Hz, 3H).

Example 12: Preparation of (4-(1-isopropyl-4-methyl-6-oxo-1,6-dihydropyridazin-3-yl)phenyl) carbonohydrazonoyl dicyanide (Compound 12)

Step 12-1: Preparation of 6-chloro-2-isopropyl-5-methylpyridazine-3(2H)-one 112 mg (yield: 43%) of the title compound was obtained in the same manner as in step 8-2 of Example 8, except that 6-chloro-5-methylpyridazine-3(2H)-one (200 mg, 1.38 mmol) was used instead of 6-chloropyridazine-3(2H)-one, and 2-iodopropane (166 μL, 1.66 mmol) was used instead of iodomethane.

$^1$H NMR (400 MHz, Chloroform-d) δ7.03 (d, J=1.2 Hz, 1H), 5.26 (p, J=6.6 Hz, 1H), 2.21 (d, J=1.3 Hz, 4H), 1.35 (d, J=6.7 Hz, 6H).

Step 12-2: Preparation of 6-(4-aminophenyl)-2-isopropyl-5-methylpyridazine-3(2H)-one 84 mg (yield: 64%) of the title compound was obtained in the same manner as in step 8-3 of Example 8, except that 6-chloro-2-isopropyl-5-methylpyridazine-3(2H)-one (100 mg, 0.53 mmol) obtained in step 12-1 above was used instead of 6-chloro-2-methylpyridazine-3(2H)-one.

$^1$H NMR (400 MHz, DMSO-$d_6$) δ7.78 (d, J=1.3 Hz, 1H), 7.59 (d, J=8.6 Hz, 2H), 6.62 (d, J=8.6 Hz, 2H), 5.45 (s, 2H), 5.20 (p, J=6.6 Hz, 1H), 2.13 (s, 2H), 1.32 (d, J=6.6 Hz, 6H).

Step 12-3: Preparation of (4-(1-isopropyl-4-methyl-6-oxo-1,6-dihydropyridazin-3-yl)phenyl)carbonohydrazonoyl dicyanide 88 mg (yield: 95%) of the title compound was obtained in the same manner as in step 1-2 of Example 1, except that 6-(4-aminophenyl)-2-isopropyl-5-methylpyridazine-3(2H)-one (70 mg, 0.29 mmol) obtained in step 12-2 above was used instead of 6-(4-aminophenyl)-2-isopropyl-4,5-dihydropyridazin-3(2H)-one.

$^1$H NMR (400 MHz, DMSO-$d_6$) δ13.13 (s, 1H), 8.03-7.93 (m, 3H), 7.57 (d, J=8.9 Hz, 2H), 5.24 (p, J=6.6 Hz, 1H), 2.16 (d, J=1.2 Hz, 3H), 1.35 (d, J=6.6 Hz, 6H).

Example 13: Preparation of (3-chloro-4-(1,4-dimethyl-6-oxo-1,6-dihydropyridazin-3-yl)phenyl)carbonohydrazonoyl dicyanide (Compound 13)

Step 13-1: Preparation of 6-(4-amino-2-chlorophenyl)-2,5-dimethylpyridazine-3(2H)-one 181 mg (yield: 77%) of the title compound was obtained in the same manner as in step 8-3 of Example 8 above, except that 4-amino-2-chlorophenylboronic acid pinacol ester (164 mg, 1.04 mmol) was used instead of 4-aminophenylboronic acid pinacol ester, and 6-chloro-2,5-dimethylpyridazine-3(2H)-one (150 mg, 0.95 mmol) obtained in step 11-1 of Example 11 above was used instead of 6-chloro-2-methylpyridazine-3(2H)-one.

$^1$H NMR (400 MHz, DMSO-$d_6$) δ7.49 (d, J=1.3 Hz, 1H), 7.16 (d, J=8.4 Hz, 1H), 6.68 (d, J=2.2 Hz, 1H), 6.57 (dd, J=8.4 Hz, 2.2 Hz, 1H), 3.68 (s, 3H), 2.11 (d, J=1.2 Hz, 3H).

Step 13-2: Preparation of (4-(1,4-dimethyl-6-oxo-1, 6-dihydropyridazin-3-yl)-3-chlorophenyl)carbonohydrazonoyl dicyanide 115 mg (yield: 59%) of the title compound was obtained in the same manner as in step 1-2 of Example 1 above, except that 6-(4-amino-2-chlorophenyl)-2,5-dimethylpyridazine-3(2H)-one (150 mg, 0.60 mmol) obtained in step 13-1 above was used instead of 6-(4-aminophenyl)-2-isopropyl-4,5-dihydropyridazin-3(2H)-one.

$^1$H NMR (400 MHz, DMSO-$d_6$) δ7.61-7.55 (m, 3H), 7.51 (dd, J=8.5 Hz, 2.1 Hz, 1H), 3.72 (s, 3H), 2.14 (d, J=1.2 Hz, 3H).

Example 14: Preparation of (4-(1,4-dimethyl-6-oxo-1,6-dihydropyridazin-3-yl)-3-fluorophenyl)carbonohydrazonoyl dicyanide (Compound 14)

Step 14-1: Preparation of 6-(4-amino-2-fluorophenyl)-2,5-dimethylpyridazine-3(2H)-one 146 mg (yield: 83%) of the title compound was obtained in the same manner as in step 8-3 of Example 8 above, except that 4-amino-2-fluorophenylboronic acid pinacol ester (197 mg, 0.83 mmol) was used instead of 4-aminophenylboronic acid pinacol ester and 6-chloro-2,5-dimethylpyridazine-3(2H)-one (120 mg, 0.76 mmol) obtained in step 11-1 of Example 11 above was used instead of 6-chloro-2-methylpyridazine-3(2H)-one.

$^1$H NMR (400 MHz, DMSO-$d_6$) δ7.55 (s, 1H), 7.34 (t, J=8.9 Hz, 1H), 6.45 (dd, J=8.4 Hz, 2.1 Hz, 1H), 6.38 (dd, J=14.3 Hz, 2.1 Hz, 1H), 5.77 (s, 2H), 3.69 (s, 3H), 2.12 (d, J=1.2 Hz, 3H).

Step 14-2: Preparation of (4-(1,4-dimethyl-6-oxo-1, 6-dihydropyridazin-3-yl)-3-fluorophenyl)carbonohydrazonoyl dicyanide 88 mg (yield: 66%) of the title compound was obtained in the same manner as in step 1-2 of Example 1 above, except that 6-(4-amino-2-fluorophenyl)-2,5-dimethylpyridazine-3(2H)-one (100 mg, 0.43 mmol) obtained in step 14-1 above was used instead of 6-(4-aminophenyl)-2-isopropyl-4,5-dihydropyridazin-3(2H)-one.

$^1$H NMR (400 MHz, DMSO-$d_6$) δ7.73 (d, J=8.6 Hz, 1H), 7.67 (s, 1H), 7.42-7.33 (m, 3H), 3.74 (s, 3H), 2.15 (s, 3H).

PREPARATION EXAMPLES

Meanwhile, the novel compound represented by Formula 1 according to the present invention may be formulated in various forms. The following examples exemplarily describe several methods of preparing formulations including the compound represented by Formula 1 according to the present invention as an active ingredient, and the present invention is not limited thereto.

Preparation Example 1: Preparation of Tablet by Direct Pressing 5.0 mg of each of the active ingredients prepared in Examples 1 to 14 was sieved, mixed with 14.1 mg of lactose, 0.8 mg of crospovidone USNF, and 0.1 mg of magnesium stearate, and then pressed into tablets.

Preparation Example 2: Preparation of Tablet by Wet Granulation 5.0 mg of each of the active ingredients prepared in Examples 1 to 14 was sieved and mixed with 16.0 mg of lactose and 4.0 mg of starch. 0.3 mg of polysorbate 80 was dissolved in pure water, and this solution was added to the mixture in a suitable amount, followed by atomizing to obtain fine particles. After drying, the fine particles were sieved, mixed with 2.7 mg of colloidal silicon dioxide and 2.0 mg of magnesium stearate, and pressed into tablets.

Preparation Example 3: Preparation of Powder and Capsule 5.0 mg of each of the active ingredients prepared in Examples 1 to 14 was sieved and then mixed with 14.8 mg of lactose, 10.0 mg of polyvinylpyrrolidone, and 0.2 mg of magnesium stearate. The mixture was filled into hard No. 5 gelatin capsules using a suitable apparatus to prepare capsules.

Preparation Example 4: Preparation of Injection Drug 100 mg of each of the active ingredients prepared in Examples 1 to 14 was mixed with 180 mg of mannitol, 26 mg of $Na_2HPO_4 \cdot 12H_2O$, and 2974 mg of distilled water to prepare injection drugs.

Experimental Example 1: Selection of Tau Protein Aggregation—Inhibiting Substance Using Cell Model In order to select novel tau protein aggregation—inhibiting substances, tau-BiFC cell model, in which formation of tau oligomers in living cells is easily observed, was used. Tau-BiFC cells were aliquoted into a 384-well plate. The next day, the cells were treated with each of the compounds prepared according to Examples 1 to 14 at concentrations of 1 μM, 3 μM, and 10 μM, together with Forskolin (at a treatment concentration of 30 μM), which is a compound inducing tau protein aggregation by activating tau phosphorylase PKA. After 48 hours, nuclei in the cells were stained using Hoechst (at a treatment concentration of 2 μg/mL), and BiFC fluorescence intensity was automatically measured using Operetta (PerkinElmer) to count stained nuclei in each well out of the entire well plate. The group treated only with Forskolin, which induces tau protein aggregation, was set to a reference point of a 100% tau protein-aggregated state, and the effects of the compounds were confirmed using the equation "BiFC fluorescence intensity due to compound synthesized according to embodiment of present invention/(fluorescence intensity of control group treated only with Forskolin inducing tau protein aggregation—fluorescence intensity of untreated control group)×100". Furthermore, the degree of cytotoxicity induced by the newly synthesized compound was also measured based on the 100% cell viability of the group treated only with Forskolin as a reference, and the cytotoxicity value of each compound was calculated using the equation "(number of stained nuclei in group treated with compound/number of stained nuclei in group treated with Forskolin)×100". Based on the treatment results, substances inhibiting intracellular tau protein aggregation were selected from a series of candidate groups showing a tau protein aggregation inhibition rate of 70% or more and a cell viability of 100% at a compound treatment concentration of 10 μM or more.

Experimental Example 2: Confirmation of Concentration-Dependent Inhibitory Effect of Novel Compound on Tau Protein Aggregation In order to evaluate dose-dependent tau protein aggregation inhibition effects of the compounds selected according to Experimental Example 1 on tau protein aggregation, tau-BiFC cells were treated with the selected compounds at concentrations of 0.03 μM, 0.01 μM, 0.3 μM, 1 μM, 3 μM, 10 μM, and 30 μM, respectively, together with Forskolin (at a treatment concentration of 30 μM), which is a tau protein aggregation-inducing substance. After 48 hours, tau protein aggregation reaction and degrees of cytotoxicity were analyzed by observing images of the cells. $IC_{50}$ and toxicity of the compounds were analyzed by nonlinear regression analysis of Prism software (Graph Pad). Calculated results of representative compounds are shown in Table 2 below. Structural formulae for compounds of comparative examples compared therewith are shown in Table 3 below.

TABLE 2

| | Tau BiFC in cells | | |
|---|---|---|---|
| Compound # | $IC_{50}$ (μM) | Response (%, @10 μM) | Cell viability (%, @10 μM) |
| Example 1 | 0.3 | 0 | 110.1 |
| Example 2 | 0.4 | 0 | 102.8 |
| Example 3 | 0.09 | 0 | 68.2 |
| Example 4 | 0.45 | 0 | 98.7 |
| Example 5 | 0.09 | 15.6 | 95.7 |
| Example 6 | 0.07 | 0 | 62.9 |
| Example 7 | 0.94 | 2.3 | 89.3 |
| Example 8 | 0.03 | 0 | 123.6 |
| Example 9 | 0.2 | 0 | 96.9 |
| Example 10 | 0.8 | 0 | 103.7 |
| Example 11 | 0.06 | 0 | 112.6 |
| Example 12 | <0.10 | 0 | 83.6 |
| Example 13 | 0.36 | 0 | 133.9 |
| Example 14 | 0.75 | 0 | 117.3 |
| Levosimendan (Reference) | 1.44 | 9.58 | 73.21 |
| Comparative Example 1 | 16.8 | 10.1 | 130.3 |
| Comparative Example 2 | 3.5 | 1.8 | 128.6 |
| Comparative Example 3 | >>10 | 37.11 | 113.1 |
| Comparative Example 4 | >10 | 45.7 | 120.3 |
| Comparative Example 5 | >10 | 35.1 | 124.2 |
| Comparative Example 6 | >10 | 46.7 | 114.9 |
| Comparative Example 7 | 4.5 | 19.4 | 102.3 |
| Comparative Example 8 | 2.5 | 0 | 110.1 |

TABLE 3

| | |
|---|---|
| Comparative Example 1 | 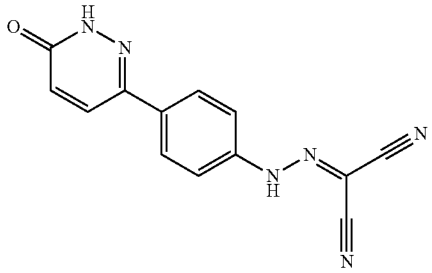 [SMILES: N#CC(C#N)=NNc1ccc(-c2ccc(=O)[nH]n2)cc1] |
| Comparative Example 2 | 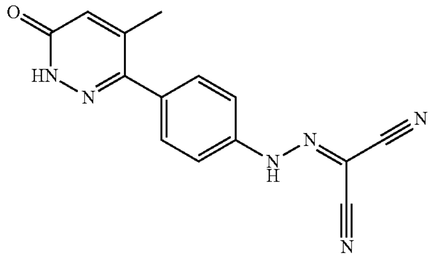 [SMILES: Cc1cc(=O)[nH]nc1-c1ccc(NN=C(C#N)C#N)cc1] |
| Comparative Example 3 | 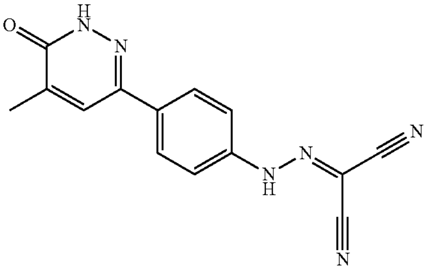 [SMILES: Cc1cc(-c2ccc(NN=C(C#N)C#N)cc2)n[nH]c1=O] |
| Comparative Example 4 | 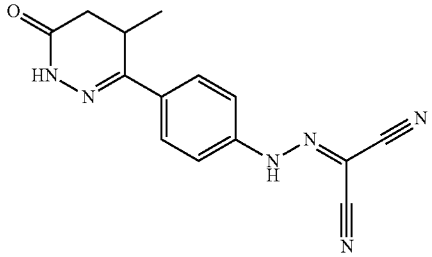 [SMILES: CC1CC(=O)NN=C1c1ccc(NN=C(C#N)C#N)cc1] |
| Comparative Example 5 | 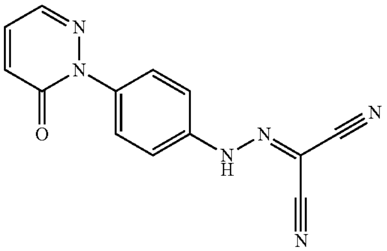 [SMILES: N#CC(C#N)=NNc1ccc(-n2ncccc2=O)cc1] |
| Comparative Example 6 | 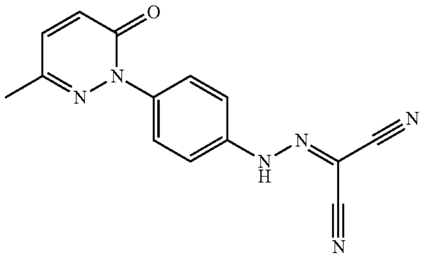 [SMILES: Cc1ccc(=O)n(-c2ccc(NN=C(C#N)C#N)cc2)n1] |

TABLE 3-continued

| | |
|---|---|
| Comparative Example 7 | 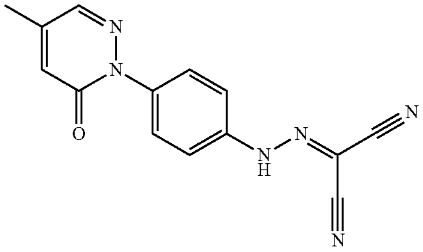 [SMILES: Cc1cnn(-c2ccc(NN=C(C#N)C#N)cc2)c(=O)c1] |
| Comparative Example 8 | 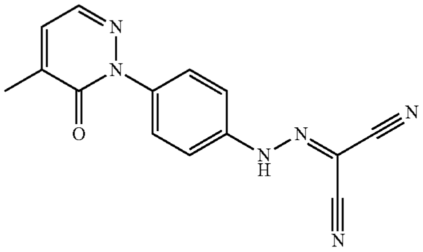 [SMILES: Cc1ccnn(-c2ccc(NN=C(C#N)C#N)cc2)c1=O] |

As shown in Tables 2 and 3, the compounds of the present invention exhibited superior inhibitory effects on tau protein aggregation compared to the known substance, Levosimendan. But, it was also confirmed that the compounds of the comparative examples which include a backbone similar to the compounds of the present invention and differ in the presence and absence of a substituent on the nitrogen atom at the 2-position of pyridazinone or 4,5-dihydropyridazinone, and the binding position thereof with a phenyl group, exhibited lower inhibitory effects on tau protein aggregation than Levosimendan, which is a reference substance.

Experimental Example 3: Inhibitory Effect of Novel Compound on CYP Coenzyme Activity The inhibitory effects of the compounds prepared according to Examples 1 to 14 on CYP coenzyme activity were identified. Specifically, human liver microsomes (0.25 mg/mL), a 0.1 M phosphate buffer solution (pH 7.4), a substrate drug cocktail of five types of drug metabolism enzymes (50 μM phenacetin, 10 μM diclofenac, 100 μM S-mephenytoin, 5 μM dextromethorphan, and 2.5 μM midazolam), and the compound at a concentration of 0 μM or 10 μM were mixed and pre-cultured at 37° C. for 5 minutes, and then further cultured at 37° C. for 15 minutes together with an NADPH generation system solution added thereto. Thereafter, the reaction was terminated by adding an acetonitrile solution containing an internal standard material (terfenadine) and centrifuged for 5 minutes (14,000 rpm, 4° C.), and then a supernatant was injected into an LC-MS/MS system for simultaneous analysis of metabolites of the substrate drugs to thereby evaluate the inhibitory effects on drug metabolism.

Metabolites of each CYP coenzyme indicator drug generated through the reaction were analyzed using the Shimadzu Nexera XR system and TSQ Vantage (Thermo). In an HPLC column, Kinetex C18 (2.1 mm×100 mm, 2.6 μm particle size; Phenomenex, USA) was used, and mobile phases were (A) distilled water containing 0.1% formic acid and (B) acetonitrile containing 0.1% formic acid, and a gradient program shown in Table 3 was applied thereto.

TABLE 3

| Time (min) | Flow rate (mL/min) | % A | % B |
|---|---|---|---|
| 0 | 0.3 | 100 | 0 |
| 1.0 | 0.3 | 60 | 40 |
| 4.0 | 0.3 | 50 | 50 |
| 4.1 | 0.3 | 100 | 0 |
| 7.0 | 0.3 | 100 | 0 |

The generated metabolites were quantified using a multiple reaction monitoring (MRM) quantification mode, and Xcalibur (version 1.6.1) was used for data analysis. In order to express the inhibitory effects of the novel compounds prepared according to the examples of the present invention on CYP coenzyme activity, CYP coenzyme activities (%) with respect to the control group not treated with any compound are shown in Table 4 below.

TABLE 4

| Compound # | CYP1A2 | CYP2C9 | CYP2C19 | CYP2D6 | CYP3A4 |
|---|---|---|---|---|---|
| 1 | 79 | 70.4 | 70.8 | 74.6 | 81.7 |
| 2 | 80.5 | 65.7 | 64.7 | 84.9 | 74.6 |
| 3 | >100 | 99.9 | >100 | 93.6 | >100 |
| 4 | 74.8 | 55.6 | 45.5 | 62.1 | 74.2 |
| 5 | 70 | 71.5 | 63.4 | 70.4 | 74.2 |
| 6 | 78.6 | 74.2 | 74.2 | 72.6 | 79.5 |
| 8 | 94.9 | 72.9 | 91 | 95 | 91.2 |
| 10 | 68.1 | 60.6 | 79.2 | 62 | 91.2 |
| 11 | 83.3 | 56.5 | 82.6 | 91.8 | 82.7 |
| 12 | 82.4 | 57.6 | 71.4 | 80.8 | >100 |
| 13 | 91.1 | 30.5 | 77.5 | 98.9 | >100 |
| 14 | 80.9 | 53.2 | 73.7 | 88.9 | 83.3 |

Experimental Example 4: Identification of Stability of Liver Microsome Due to Novel Compound The stability of liver microsomes due to the compounds prepared according to Examples 1 to 14 was confirmed. Specifically, four types of liver microsomes (human, dog, rat, and mouse, each 0.25 mg/mL), a 0.1 M phosphate buffer solution (pH 7.4), and each of the compounds at a concentration of 1 μM were mixed and pre-cultured at 37° C. for 5 minutes and further cultured at 37° C. for 30 minutes together with an NADPH generation system solution added thereto. Thereafter, the reaction was terminated by adding an acetonitrile solution containing an internal standard material (chlorpropamide) and centrifuged for 5 minutes (14,000 rpm, 4° C.), and then a supernatant was injected into an LC-MS/MS system for analysis of substrate drugs to thereby evaluate metabolic stability due to 8 types of compounds.

The amount of the substrate remaining after the reaction was analyzed using the Shimadzu Nexera XR system and TSQ Vantage (Thermo). In an HPLC column, Kinetex XB-C18 (2.1 mm×100 mm, particle size of 2.6 μm; Phenomenex, USA) was used, and mobile phases were (A) distilled water containing 0.1% formic acid and (B) acetonitrile containing 0.1% formic acid. Analyst software (version 1.6.3) and Xcalibur (version 1.6.1) were used for data analysis. The calculated results are shown in Table 5 below.

TABLE 5

| Compound # | Human (%) | Dog (%) | Rat (%) | Mouse (%) |
|---|---|---|---|---|
| 1 | 6.4 | >100 | >100 | >100 |
| 2 | 63.6 | >100 | 92.5 | 89 |
| 3 | 90.3 | 91.9 | 89.6 | 89.6 |
| 4 | 98.2 | 95.6 | 96.8 | 89 |
| 5 | 30.9 | >100 | 90.9 | 94.9 |
| 6 | 85 | 99.5 | 95.8 | 92.7 |
| 8 | >100 | >100 | >100 | >100 |
| 9 | 8.2 | >100 | 98.5 | 98.5 |
| 10 | 98 | 98.5 | >100 | 99.8 |
| 11 | >100 | >100 | >100 | >100 |
| 12 | 17.1 | >100 | 99.9 | 95.7 |
| 13 | 95.7 | >100 | 84.5 | 94.5 |
| 14 | 99.6 | 93.3 | 86.4 | 89.7 |

The above description of the present invention is provided for the purpose of illustration, and it would be understood by those skilled in the art that various changes and modifications may be made without changing the technical conception and essential features of the present invention. Thus, it is clear that the above-described embodiments are illustrative in all aspects and do not limit the present invention. The various embodiments disclosed herein are not intended to be limiting, with the true scope and spirit being indicated by the following claims. The present invention is to be limited only by the terms of the appended claims, along with the full scope of equivalents to which such claims are entitled.

The invention claimed is:

1. A compound represented by Formula 1 below or a pharmaceutically acceptable salt thereof:

[Formula 1]

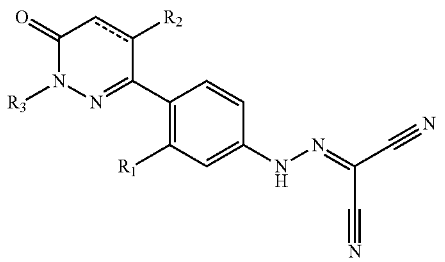

wherein in Formula 1,

------ is —or ═;

$R_1$ is hydrogen or halogen;

$R_2$ is hydrogen, or $C_{1-6}$ alkyl; and $R_3$ is $C_{1-6}$ alkyl, $C_{1-6}$ alkoxy-$C_{3-6}$ alkyl, $C_{1-6}$ haloalkyl, $C_{3-6}$ cycloalkyl, or $C_{1-6}$ alkoxy-$C_{6-10}$ aryl, with the exception if ------ is —, $R_1$ and $R_2$ are hydrogen, and $R_3$ methyl.

2. The compound or pharmaceutical salt thereof of claim 1, wherein $R_1$ is hydrogen, chloro, or fluoro;

$R_2$ is hydrogen, or methyl; and $R_3$ is methyl, ethyl, isopropyl, cyclopropyl, difluoromethyl, 2,2,2-trifluoroethyl, methoxyphenyl, or methoxyethyl.

3. The compound or pharmaceutical salt thereof of claim 1, wherein the compound is represented by Formula 2 or Formula 3 below:

[Formula 2]

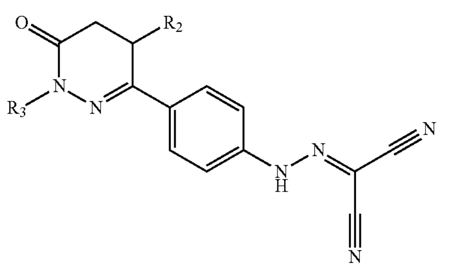

[Formula 3]

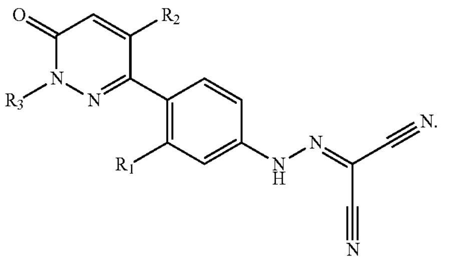

4. The compound or pharmaceutical salt thereof of claim 1, wherein the compound is 1) (4-(1-isopropyl-6-oxo-1,4,5,6-tetrahydropyridazin-3-yl)phenyl) carbonohydrazonoyl dicyanide,
2) (4-(1-isopropyl-4-methyl-6-oxo-1,4,5,6-tetrahydropyridazin-3-yl)phenyl) carbonohydrazonoyl dicyanide,
3) (4-(1-ethyl-4-methyl-6-oxo-1,4,5,6-tetrahydropyridazin-3-yl)phenyl) carbonohydrazonoyl dicyanide,
4) (4-(4-methyl-6-oxo-1-(2,2,2-trifluoroethyl)-1,4,5,6-tetrahydropyridazin-3-yl)phenyl) carbonohydrazonoyl dicyanide,
5) (4-(1-(2-methoxyethyl)-4-methyl-6-oxo-1,4,5,6-tetrahydropyridazin-3-yl)phenyl) carbonohydrazonoyl dicyanide,
6) (4-(1-cyclopropyl-4-methyl-6-oxo-1,4,5,6-tetrahydropyridazin-3-yl)phenyl) carbonohydrazonoyl dicyanide,
7) (4-(1-(4-methoxyphenyl)-4-methyl-6-oxo-1,4,5,6-tetrahydropyridazin-3-yl)phenyl) carbonohydrazonoyl dicyanide,
8) (4-(1-methyl-6-oxo-1,6-dihydropyridazin-3-yl)phenyl) carbonohydrazonoyl dicyanide,
9) (4-(1-isopropyl-6-oxo-1,6-dihydropyridazin-3-yl)phenyl) carbonohydrazonoyl dicyanide,
10) (4-(1-(difluoromethyl)-6-oxo-1,6-dihydropyridazin-3-yl)phenyl) carbonohydrazonoyl dicyanide,
11) (4-(1,4-dimethyl-6-oxo-1,6-dihydropyridazin-3-yl) phenyl) carbonohydrazonoyl dicyanide,
12) (4-(1-isopropyl-4-methyl-6-oxo-1,6-dihydropyridazin-3-yl)phenyl) carbonohydrazonoyl dicyanide,
13) (3-chloro-4-(1,4-dimethyl-6-oxo-1,6-dihydropyridazin-3-yl)phenyl) carbonohydrazonoyl dicyanide, or
14) (4-(1,4-dimethyl-6-oxo-1,6-dihydropyridazin-3-yl)-3-fluorophenyl) carbonohydrazonoyl dicyanide.

5. A method of preparing the compound according to claim 1, the method comprising:

reacting a compound represented by Formula 4 below including a reactive amine group at one end with sodium nitrite and malononitrile in the presence of an acid to form an imine bond:

[Formula 4]

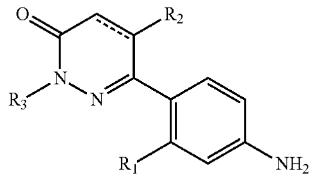

wherein in Formula 4 above, $R_1$ to $R_3$ are as defined in claim 1.

6. The method of claim 5, wherein the method is performed via a series of processes comprising:

a first step of dissolving the compound of Formula 4 and sodium nitrite in a $C_{1-4}$ lower alcohol solvent and adding an aqueous acid solution thereto at a temperature of −5° C. to 5° C. to form a diazonium salt, a second step of adding malononitrile to a reaction solution including the diazonium salt obtained in the first step and performing a reaction at a temperature of 15° C. to 40° C., and a third step of adding an aqueous base solution to the reaction solution of the second step for neutralization.

7. The method of claim 5, wherein the compound of Formula 4 above is a compound represented by Formula 4-a or 4-b below:

[Formula 4-a]

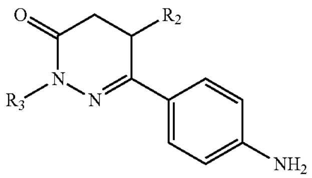

[Formula 4-b]

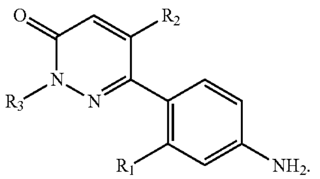

8. The method of claim 7, wherein the compound represented by Formula 4-a is prepared via a series of processes comprising the steps of:

a-1) reacting 4-(4-acetamidophenyl-4-oxo-(unsubstituted or $R_2$-substituted)-butanoic acid with hydrazine, a-2) reacting N-(6-oxo-(unsubstituted or $R_2$-substituted)-1,4,5,6-tetrahydropyridazin-3-yl)phenyl) acetamide obtained in the previous step with an acid, and a-3) reacting 6-(4-aminophenyl-(unsubstituted or $R_2$-substituted)-4,5-dihydropyridazin-3 (2H)-one obtained in the previous step with $R_3X$ (where X is halogen) under basic conditions optionally when $R_3$ is a substituent other than hydrogen, or step a-1') reacting 4-(4-aminophenyl)-4-oxo-(unsubstituted or $R_2$-substituted)-butanoic acid with unsubstituted or $R_3$-substituted hydrazine.

9. The method of claim 7, wherein the compound represented by Formula 4-b above is prepared via a series of processes comprising the steps of:

b-1) reacting by dissolving 3,6-dihalo(unsubstituted or $R_2$-substituted)pyridazine in an acid, and solidifying by adding a base thereto, b-2) reacting 6-halo-(unsubstituted or $R_2$-substituted) pyridazine-3 (2H)-one prepared in the previous step with $R_3X$ (where X is halogen) under basic conditions optionally when $R_3$ is a substituent other than hydrogen, b-3) reacting 6-halo-2-(unsubstituted or $R_3$-substituted)-(unsubstituted or $R_2$-substituted)pyridazine-3 (2H)-one obtained in the previous step with 4-amino or nitro-(unsubstituted or $R_1$-substituted phenyl) boronic acid pinacol ester in the presence of a $Pd(PPh_3)_2$ catalyst, and b-4) reacting the compound having a nitro substituent at one end thereof obtained in the previous step in the presence of a Pd/C catalyst under a hydrogen atmosphere to reduce the nitro group to an amine group, optionally, when reaction is performed with 4-nitro-(unsubstituted or $R_1$-substituted phenyl) boronic acid pinacol ester in step b-3.

10. A composition for inhibiting aggregation of tau protein comprising the compound according to claim 1 as an active ingredient.

11. A composition for inhibiting hyperphosphorylation of tau protein comprising the compound according to claim 1 as an active ingredient.

12. A pharmaceutical composition for treating a disease caused by aggregation or hyperphosphorylation of tau protein comprising the compound according to claim 1 as an active ingredient.

13. The pharmaceutical composition of claim 12, wherein the disease caused by aggregation or hyperphosphorylation of tau protein is selected from the group consisting of Alzheimer's disease, Parkinson's disease, vascular dementia, acute stroke, trauma, cerebrovascular disease, brain cord trauma, spinal cord trauma, peripheral neuropathy, retinopathy, glaucoma, and tauopathy.

14. The pharmaceutical composition of claim 13, wherein the tauopathy is selected from the group consisting of chronic traumatic encephalopathy (CTE), primary age-related tauopathy, progressive supranuclear palsy, corticobasal degeneration, Pick's disease, argyrophilic grain disease (AGD), frontotemporal dementia (FTD), Parkinsonism linked to chromosome 17, Lytico-bodig disease (Parkinsonism-dementia complex of Guam), ganglioglioma, gangliocytoma, meningioangiomatosis, postencephalitic Parkinsonism, subacute sclerosing panencephalitis, lead encephalopathy, tuberous sclerosis, pantothenate kinase-associated neurodegeneration, lipofuscinosis, and traumatic brain injury.

15. The compound or pharmaceutical salt thereof of claim 2, wherein the compound is represented by Formula 2 or Formula 3 below:

[Formula 2]

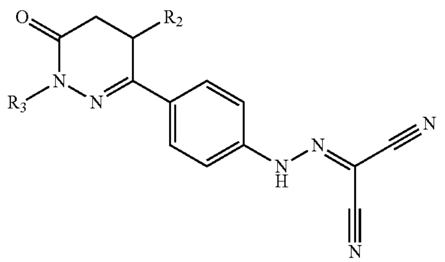

[Formula 3]

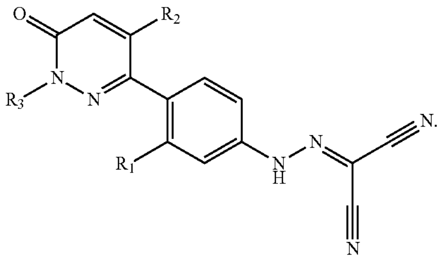

* * * * *